(12) United States Patent
Kroll et al.

(10) Patent No.: US 9,895,168 B2
(45) Date of Patent: *Feb. 20, 2018

(54) SPINAL CORRECTION SYSTEM ACTUATORS

(71) Applicant: K2M, Inc., Leesburg, VA (US)

(72) Inventors: Ryan M. Kroll, Mount Pleasant, SC (US); Steven J. Seme, Savage, MN (US); Thomas J. Gisel, Chaska, MN (US); Mark W. Kroll, Crystal Bay, MN (US)

(73) Assignee: K2M, Inc., Leesburg, VA (US)

( * ) Notice: Subject to any disclaimer, the term of this patent is extended or adjusted under 35 U.S.C. 154(b) by 90 days.

This patent is subject to a terminal disclaimer.

(21) Appl. No.: 15/010,036

(22) Filed: Jan. 29, 2016

(65) Prior Publication Data

US 2016/0220276 A1 Aug. 4, 2016

Related U.S. Application Data

(63) Continuation of application No. 14/123,729, filed as application No. PCT/US2012/040493 on Jun. 1, 2012, now Pat. No. 9,333,009.

(60) Provisional application No. 61/493,117, filed on Jun. 3, 2011.

(51) Int. Cl.
*A61B 17/70* (2006.01)
*A61B 17/00* (2006.01)

(52) U.S. Cl.
CPC ...... *A61B 17/7002* (2013.01); *A61B 17/7014* (2013.01); *A61B 17/7016* (2013.01); *A61B 17/7041* (2013.01); *A61B 17/7053* (2013.01); *A61B 17/7083* (2013.01); *A61B 17/7067* (2013.01); *A61B 2017/00221* (2013.01)

(58) Field of Classification Search
CPC ............ A61B 17/7002; A61B 17/7014; A61B 17/7016; A61B 17/7041; A61B 17/7053; A61B 17/7064; A61B 17/7083
USPC ................................ 242/393–394, 371, 379
See application file for complete search history.

(56) References Cited

U.S. PATENT DOCUMENTS

| | | |
|---|---|---|
| 2,774,350 A | 9/1952 | Cleveland |
| 3,242,922 A | 3/1966 | Thomas |
| 3,352,226 A | 11/1967 | Nelsen |
| 3,648,691 A | 3/1972 | Lumb et al. |
| 3,693,616 A | 9/1972 | Roaf et al. |

(Continued)

FOREIGN PATENT DOCUMENTS

| | | |
|---|---|---|
| DE | 2644735 A1 | 4/1977 |
| DE | 2845647 A1 | 5/1980 |

(Continued)

OTHER PUBLICATIONS

Japanese Office Action dated May 24, 2016, issued in Japanese Application No. 2014-513753.

(Continued)

*Primary Examiner* — Jacqueline Johanas
(74) *Attorney, Agent, or Firm* — Carter, DeLuca, Farrell & Schmidt, LLP

(57) ABSTRACT

A spinal correction system for implantation in a patient, the system including a reciprocating adjuster and/or a resistance adjuster coupled to a stabilizing member, for example. The resistance adjuster includes a potential energy drive, a slide unit, and a resistance unit. The reciprocating adjuster includes a piston unit, a transfer unit coupled to the piston unit, and a return mechanism.

6 Claims, 26 Drawing Sheets

(56) References Cited

U.S. PATENT DOCUMENTS

| | | |
|---|---|---|
| 3,865,105 A | 2/1975 | Lode |
| 4,024,588 A | 5/1977 | Janssen et al. |
| 4,078,559 A | 3/1978 | Nissinen |
| 4,257,409 A | 3/1981 | Bacal et al. |
| 4,269,178 A | 5/1981 | Keene |
| 4,274,401 A | 6/1981 | Miskew |
| 4,355,645 A | 10/1982 | Mitani et al. |
| 4,361,141 A | 11/1982 | Tanner |
| 4,369,769 A | 1/1983 | Edwards |
| 4,404,967 A | 9/1983 | Bacal et al. |
| 4,411,259 A | 10/1983 | Drummond |
| 4,411,545 A | 10/1983 | Roberge |
| 4,448,191 A | 5/1984 | Rodnyansky et al. |
| 4,505,268 A | 3/1985 | Sgandurra |
| 4,554,914 A | 11/1985 | Kapp et al. |
| 4,573,454 A | 3/1986 | Hoffman |
| 4,604,995 A | 8/1986 | Stephens et al. |
| 4,611,581 A | 9/1986 | Steffee |
| 4,611,582 A | 9/1986 | Duff |
| 4,634,445 A | 1/1987 | Helal |
| 4,648,388 A | 3/1987 | Steffee |
| 4,653,481 A | 3/1987 | Howland et al. |
| 4,658,809 A | 4/1987 | Ulrich et al. |
| 4,697,582 A | 10/1987 | William |
| 4,738,251 A | 4/1988 | Plaza |
| 4,773,402 A | 9/1988 | Asher et al. |
| 4,805,602 A | 2/1989 | Puno et al. |
| 4,815,453 A | 3/1989 | Cotrel |
| 4,827,918 A | 5/1989 | Olerud |
| 4,854,311 A | 8/1989 | Steffee |
| 4,931,055 A | 6/1990 | Bumpus et al. |
| 4,936,848 A | 6/1990 | Bagby |
| 5,000,166 A | 3/1991 | Karpf |
| 5,005,562 A | 4/1991 | Cotrel |
| 5,011,484 A | 4/1991 | Breard |
| 5,030,220 A | 7/1991 | Howland |
| 5,042,982 A | 8/1991 | Harms et al. |
| 5,084,049 A | 1/1992 | Asher et al. |
| 5,092,866 A | 3/1992 | Breard et al. |
| 5,092,867 A | 3/1992 | Harms et al. |
| 5,127,912 A | 7/1992 | Ray et al. |
| 5,129,900 A | 7/1992 | Asher et al. |
| 5,133,716 A | 7/1992 | Plaza |
| 5,147,363 A | 9/1992 | Harle |
| 5,176,679 A | 1/1993 | Lin |
| 5,176,680 A | 1/1993 | Vignaud et al. |
| 5,181,917 A | 1/1993 | Rogozinski |
| 5,190,543 A | 3/1993 | Schlapfer |
| 5,196,014 A | 3/1993 | Lin |
| 5,207,678 A | 5/1993 | Harms et al. |
| 5,209,752 A | 5/1993 | Ashman et al. |
| 5,219,349 A | 6/1993 | Krag et al. |
| 5,242,443 A | 9/1993 | Kambin |
| 5,254,118 A | 10/1993 | Mirkovic |
| 5,257,994 A | 11/1993 | Lin |
| 5,259,398 A | 11/1993 | Vrespa |
| 5,282,862 A | 2/1994 | Baker et al. |
| 5,306,275 A | 4/1994 | Bryan |
| 5,312,404 A | 5/1994 | Asher et al. |
| 5,312,410 A | 5/1994 | Miller et al. |
| 5,312,420 A | 5/1994 | Toso et al. |
| 5,330,473 A | 7/1994 | Howland |
| 5,330,474 A | 7/1994 | Lin |
| 5,352,226 A | 10/1994 | Lin |
| 5,360,431 A | 11/1994 | Puno et al. |
| 5,366,455 A | 11/1994 | Dove et al. |
| 5,368,594 A | 11/1994 | Martin et al. |
| 5,380,323 A | 1/1995 | Howland |
| 5,380,325 A | 1/1995 | Lahille et al. |
| 5,382,248 A | 1/1995 | Jacobson et al. |
| 5,387,212 A | 2/1995 | Yuan et al. |
| 5,387,213 A | 2/1995 | Breard et al. |
| 5,391,168 A | 2/1995 | Sanders et al. |
| 5,397,363 A | 3/1995 | Gelbard |
| 5,413,576 A | 5/1995 | Rivard |
| 5,436,542 A | 7/1995 | Petelin et al. |
| 5,437,669 A | 8/1995 | Yuan et al. |
| 5,437,671 A | 8/1995 | Lozier et al. |
| 5,456,722 A | 10/1995 | McLeod et al. |
| 5,466,238 A | 11/1995 | Lin |
| 5,470,333 A | 11/1995 | Ray |
| 5,480,440 A | 1/1996 | Kambin |
| 5,486,174 A | 1/1996 | Fournet-Fayard et al. |
| 5,487,744 A | 1/1996 | Howland |
| 5,490,851 A | 2/1996 | Nenov et al. |
| 5,496,318 A | 3/1996 | Howland et al. |
| 5,498,262 A | 3/1996 | Bryan |
| 5,501,684 A | 3/1996 | Schlapfer et al. |
| 5,520,688 A | 5/1996 | Lin |
| 5,527,314 A | 6/1996 | Brumfield et al. |
| 5,534,002 A | 7/1996 | Brumfield et al. |
| 5,540,689 A | 7/1996 | Sanders et al. |
| 5,544,993 A | 8/1996 | Harle |
| 5,549,679 A | 8/1996 | Kuslich |
| 5,562,660 A | 10/1996 | Grob |
| 5,562,662 A | 10/1996 | Brumfield et al. |
| 5,569,246 A | 10/1996 | Ojima et al. |
| 5,571,191 A | 11/1996 | Fitz |
| 5,575,791 A | 11/1996 | Lin |
| 5,584,626 A | 12/1996 | Assmundson |
| 5,586,983 A | 12/1996 | Sanders et al. |
| 5,591,165 A | 1/1997 | Jackson |
| 5,601,554 A | 2/1997 | Howland et al. |
| 5,609,592 A | 3/1997 | Brumfield et al. |
| 5,611,800 A | 3/1997 | Davis et al. |
| 5,620,443 A | 4/1997 | Gertzbein et al. |
| 5,630,816 A | 5/1997 | Kambin |
| 5,643,259 A | 7/1997 | Sasso et al. |
| 5,645,599 A | 7/1997 | Samani |
| 5,649,926 A | 7/1997 | Howland |
| 5,658,284 A | 8/1997 | Sebastian et al. |
| 5,672,175 A | 9/1997 | Martin |
| 5,676,703 A | 10/1997 | Gelbard |
| 5,702,395 A | 12/1997 | Hopf |
| 5,702,399 A | 12/1997 | Kilpela et al. |
| 5,702,452 A | 12/1997 | Argenson et al. |
| 5,704,936 A | 1/1998 | Mazel |
| 5,713,898 A | 2/1998 | Stucker et al. |
| 5,716,355 A | 2/1998 | Jackson et al. |
| 5,720,746 A | 2/1998 | Soubeiran |
| 5,725,582 A | 3/1998 | Bevan et al. |
| 5,728,097 A | 3/1998 | Mathews |
| 5,733,284 A | 3/1998 | Martin |
| 5,735,852 A | 4/1998 | Amrein et al. |
| 5,782,831 A | 7/1998 | Sherman et al. |
| 5,797,910 A | 8/1998 | Martin |
| 5,810,817 A | 9/1998 | Roussouly et al. |
| 5,810,819 A | 9/1998 | Errico et al. |
| 5,814,046 A | 9/1998 | Hopf |
| 5,885,285 A | 3/1999 | Simonson |
| 5,891,145 A | 4/1999 | Morrison et al. |
| 5,902,305 A | 5/1999 | Beger et al. |
| 5,910,142 A | 6/1999 | Tatar |
| 5,928,232 A | 7/1999 | Howland et al. |
| 5,938,663 A | 8/1999 | Petreto |
| 5,947,967 A | 9/1999 | Barker |
| 5,964,769 A | 10/1999 | Wagner et al. |
| 5,976,135 A | 11/1999 | Sherman et al. |
| 5,980,521 A | 11/1999 | Montague et al. |
| 5,984,924 A | 11/1999 | Asher et al. |
| 5,989,256 A | 11/1999 | Kuslich et al. |
| 6,015,409 A | 1/2000 | Jackson |
| 6,033,412 A | 3/2000 | Losken et al. |
| 6,039,738 A | 3/2000 | Sanders et al. |
| 6,053,921 A | 4/2000 | Wagner et al. |
| 6,066,140 A | 5/2000 | Gertzbein et al. |
| 6,077,268 A | 6/2000 | Farris et al. |
| 6,080,156 A | 6/2000 | Asher et al. |
| 6,083,224 A | 7/2000 | Gertzbein et al. |
| 6,086,590 A | 7/2000 | Margulies et al. |
| 6,101,678 A | 8/2000 | Malloy et al. |
| 6,110,173 A | 8/2000 | Thomas, Jr. |
| 6,123,706 A | 9/2000 | Lange |
| 6,132,431 A | 10/2000 | Nilsson et al. |

(56) References Cited

U.S. PATENT DOCUMENTS

| | | |
|---|---|---|
| 6,132,464 A | 10/2000 | Martin |
| 6,136,000 A | 10/2000 | Louis et al. |
| 6,176,861 B1 | 1/2001 | Bernstein et al. |
| 6,231,575 B1 | 5/2001 | Krag |
| 6,248,106 B1 | 6/2001 | Ferree |
| 6,251,111 B1 | 6/2001 | Barker et al. |
| 6,254,603 B1 | 7/2001 | Gertzbein et al. |
| 6,261,288 B1 | 7/2001 | Jackson |
| 6,273,914 B1 | 8/2001 | Papas |
| 6,277,120 B1 | 8/2001 | Lawson |
| 6,283,967 B1 | 9/2001 | Troxell et al. |
| 6,293,949 B1 | 9/2001 | Justis et al. |
| 6,296,643 B1 | 10/2001 | Hopf et al. |
| 6,299,613 B1 | 10/2001 | Ogilvie et al. |
| 6,325,805 B1 | 12/2001 | Ogilvie et al. |
| 6,328,739 B1 | 12/2001 | Liu et al. |
| 6,358,254 B1 | 3/2002 | Anderson |
| 6,364,883 B1 | 4/2002 | Santilli |
| 6,364,885 B1 | 4/2002 | Kilpela et al. |
| 6,391,030 B1 | 5/2002 | Wagner et al. |
| 6,402,749 B1 | 6/2002 | Ashman |
| 6,402,752 B2 | 6/2002 | Schaffler-Wachter et al. |
| 6,419,703 B1 | 7/2002 | Fallin et al. |
| 6,423,065 B2 | 7/2002 | Ferree |
| 6,451,019 B1 | 9/2002 | Zucherman et al. |
| 6,458,131 B1 | 10/2002 | Ray |
| 6,471,704 B2 | 10/2002 | Gertzbein et al. |
| 6,488,683 B2 | 12/2002 | Lieberman |
| 6,514,255 B1 | 2/2003 | Ferree |
| 6,520,962 B1 | 2/2003 | Taylor et al. |
| 6,537,276 B2 | 3/2003 | Metz-Stavenhagen |
| 6,547,789 B1 | 4/2003 | Ventre et al. |
| 6,551,320 B2 | 4/2003 | Lieberman |
| 6,554,831 B1 | 4/2003 | Rivard et al. |
| 6,562,038 B1 | 5/2003 | Morrison |
| 6,565,569 B1 | 5/2003 | Assaker et al. |
| 6,565,605 B2 | 5/2003 | Goble et al. |
| 6,569,164 B1 | 5/2003 | Assaker et al. |
| 6,579,292 B2 | 6/2003 | Taylor |
| 6,579,319 B2 | 6/2003 | Goble et al. |
| 6,582,433 B2 | 6/2003 | Yun |
| 6,585,738 B1 | 7/2003 | Mangione et al. |
| 6,589,243 B1 | 7/2003 | Viart et al. |
| 6,602,254 B2 | 8/2003 | Gertzbein et al. |
| 6,602,818 B2 | 8/2003 | Choi et al. |
| 6,610,091 B1 | 8/2003 | Reiley |
| 6,616,669 B2 | 9/2003 | Ogilvie et al. |
| 6,623,484 B2 | 9/2003 | Betz et al. |
| 6,626,906 B1 | 9/2003 | Young |
| 6,626,909 B2 | 9/2003 | Chin |
| 6,641,585 B2 | 11/2003 | Sato et al. |
| 6,645,207 B2 | 11/2003 | Dixon et al. |
| 6,651,320 B1 | 11/2003 | Yagi et al. |
| 6,656,185 B2 | 12/2003 | Gleason et al. |
| 6,669,729 B2 | 12/2003 | Chin |
| 6,682,532 B2 | 1/2004 | Johnson et al. |
| 6,682,533 B1 | 1/2004 | Dinsdale et al. |
| 6,685,705 B1 | 2/2004 | Taylor |
| 6,689,133 B2 | 2/2004 | Morrison et al. |
| 6,709,435 B2 | 3/2004 | Lin |
| 6,736,817 B2 | 5/2004 | Troxell et al. |
| 6,749,612 B1 | 6/2004 | Conchy et al. |
| 6,755,828 B2 | 6/2004 | Shevtsov et al. |
| 6,773,437 B2 | 8/2004 | Ogilvie et al. |
| 6,802,844 B2 | 10/2004 | Ferree |
| 6,811,567 B2 | 11/2004 | Reiley |
| 6,835,207 B2 | 12/2004 | Zacouto et al. |
| 6,840,127 B2 | 1/2005 | Moran |
| 6,860,884 B2 | 3/2005 | Shirado et al. |
| 6,887,241 B1 | 5/2005 | McBride et al. |
| 6,902,580 B2 | 6/2005 | Fallin et al. |
| 6,946,000 B2 | 9/2005 | Senegas et al. |
| 6,966,910 B2 | 11/2005 | Ritland |
| 6,966,930 B2 | 11/2005 | Amin et al. |
| 6,974,478 B2 | 12/2005 | Reiley et al. |
| 6,986,771 B2 | 1/2006 | Paul et al. |
| 7,008,423 B2 | 3/2006 | Assaker et al. |
| 7,018,379 B2 | 3/2006 | Drewry et al. |
| 7,029,475 B2 | 4/2006 | Panjabi |
| 7,041,136 B2 | 5/2006 | Goble et al. |
| 7,048,736 B2 | 5/2006 | Robinson et al. |
| 7,051,451 B2 | 5/2006 | Augostino et al. |
| 7,074,237 B2 | 7/2006 | Goble et al. |
| 7,083,621 B2 | 8/2006 | Shaolian et al. |
| 7,087,056 B2 | 8/2006 | Vaughan |
| 7,090,698 B2 | 8/2006 | Goble et al. |
| 7,104,992 B2 | 9/2006 | Bailey |
| RE39,325 E | 10/2006 | Bryan |
| 7,128,743 B2 | 10/2006 | Metz-Stavenhagen |
| 7,137,986 B2 | 11/2006 | Troxell et al. |
| 7,160,312 B2 | 1/2007 | Saadat |
| 7,220,262 B1 | 5/2007 | Hynes |
| 7,261,714 B2 | 8/2007 | Richelsoph |
| 7,270,665 B2 | 9/2007 | Morrison et al. |
| 7,290,347 B2 | 11/2007 | Augostino et al. |
| 7,294,129 B2 | 11/2007 | Hawkins et al. |
| 7,316,684 B1 | 1/2008 | Baccelli et al. |
| 7,335,203 B2 | 2/2008 | Winslow et al. |
| 7,338,490 B2 | 3/2008 | Ogilvie et al. |
| 7,344,539 B2 | 3/2008 | Serhan et al. |
| 7,361,196 B2 | 4/2008 | Fallin et al. |
| 7,367,978 B2 | 5/2008 | Drewry et al. |
| 7,406,775 B2 | 8/2008 | Funk et al. |
| 7,445,635 B2 | 11/2008 | Fallin et al. |
| 7,473,267 B2 | 1/2009 | Nguyen et al. |
| 7,473,269 B1 | 1/2009 | Hynes |
| 7,481,828 B2 | 1/2009 | Mazda et al. |
| 7,507,242 B2 | 3/2009 | Triplett et al. |
| 7,524,324 B2 | 4/2009 | Winslow et al. |
| 7,566,345 B1 | 7/2009 | Fallin et al. |
| 7,588,578 B2 | 9/2009 | Triplett et al. |
| 7,588,590 B2 | 9/2009 | Chervitz et al. |
| 7,591,836 B2 | 9/2009 | Dick et al. |
| 7,594,924 B2 | 9/2009 | Albert et al. |
| 7,611,526 B2 | 11/2009 | Carl et al. |
| 7,618,453 B2 | 11/2009 | Goble et al. |
| 7,618,455 B2 | 11/2009 | Goble et al. |
| 7,621,955 B2 | 11/2009 | Goble et al. |
| 7,648,521 B2 | 1/2010 | Hestad |
| 7,658,753 B2 | 2/2010 | Carl et al. |
| 7,674,293 B2 | 3/2010 | Kuiper et al. |
| 7,678,136 B2 | 3/2010 | Doubler et al. |
| 7,691,145 B2 | 4/2010 | Reiley et al. |
| 7,708,762 B2 | 5/2010 | McCarthy et al. |
| 7,717,940 B2 | 5/2010 | Woods et al. |
| 7,717,942 B2 | 5/2010 | Schumacher |
| 7,722,647 B1 | 5/2010 | Wang et al. |
| 7,722,648 B2 | 5/2010 | Drewry et al. |
| 7,753,937 B2 | 7/2010 | Chervitz et al. |
| 7,758,581 B2 | 7/2010 | Chervitz et al. |
| 7,771,474 B2 | 8/2010 | Cordaro |
| 7,794,476 B2 | 9/2010 | Wisnewski |
| 7,794,478 B2 | 9/2010 | Nilsson |
| 7,799,054 B2 | 9/2010 | Kwak et al. |
| 7,819,902 B2 | 10/2010 | Abdelgany et al. |
| 7,833,252 B2 | 11/2010 | Justis et al. |
| 7,837,714 B2 | 11/2010 | Drewry et al. |
| 7,842,071 B2 | 11/2010 | Hawkes |
| 7,862,586 B2 | 1/2011 | Malek |
| 7,896,906 B2 | 3/2011 | Kwak et al. |
| 7,918,876 B2 | 4/2011 | Mueller et al. |
| 7,927,359 B2 | 4/2011 | Trautwein et al. |
| 7,931,676 B2 | 4/2011 | Veldman et al. |
| 7,935,134 B2 | 5/2011 | Reglos et al. |
| 7,942,902 B2 | 5/2011 | Schwab |
| 7,959,653 B2 | 6/2011 | Thramann et al. |
| 7,963,978 B2 | 6/2011 | Winslow et al. |
| 7,985,243 B2 | 7/2011 | Winslow et al. |
| 8,012,184 B2 | 9/2011 | Schlapfer et al. |
| 8,016,860 B2 | 9/2011 | Carl et al. |
| 8,021,400 B2 | 9/2011 | Marino et al. |
| 8,029,543 B2 | 10/2011 | Young et al. |
| 8,029,546 B2 | 10/2011 | Capote et al. |
| 8,034,078 B2 | 10/2011 | Laskowitz et al. |

(56) References Cited

U.S. PATENT DOCUMENTS

| | | |
|---|---|---|
| 8,034,084 B2 | 10/2011 | Landry et al. |
| 8,043,345 B2 | 10/2011 | Carl et al. |
| 8,048,113 B2 | 11/2011 | Winslow et al. |
| 8,052,722 B2 | 11/2011 | Winslow et al. |
| 8,057,472 B2 | 11/2011 | Walker et al. |
| 8,066,743 B2 | 11/2011 | Young et al. |
| 8,070,775 B2 | 12/2011 | Winslow et al. |
| 8,070,776 B2 | 12/2011 | Winslow et al. |
| 8,075,594 B2 | 12/2011 | Purcell |
| 8,097,022 B2 | 1/2012 | Marik |
| 8,114,134 B2 | 2/2012 | Winslow et al. |
| 8,114,158 B2 | 2/2012 | Carl et al. |
| 8,118,837 B2 | 2/2012 | Lemoine |
| 8,147,524 B2 | 4/2012 | Piza Vallespir |
| 8,162,979 B2 | 4/2012 | Sachs et al. |
| 8,167,908 B2 | 5/2012 | Ely et al. |
| 8,192,471 B2 | 6/2012 | Ludwig et al. |
| 8,221,466 B2 | 7/2012 | Asaad et al. |
| 8,262,696 B2 | 9/2012 | Falahee |
| 8,292,934 B2 | 10/2012 | Justis et al. |
| 8,323,319 B2 | 12/2012 | Mazda et al. |
| 8,353,934 B2 | 1/2013 | Drewry et al. |
| 8,357,182 B2 | 1/2013 | Seme |
| 8,357,183 B2 | 1/2013 | Seme et al. |
| 8,361,117 B2 | 1/2013 | Michielli et al. |
| 8,403,958 B2 | 3/2013 | Schwab |
| 8,414,614 B2 | 4/2013 | Firkins et al. |
| 8,414,617 B2 | 4/2013 | Young et al. |
| 8,470,001 B2 | 6/2013 | Trautwein et al. |
| RE44,392 E | 7/2013 | Hynes |
| 8,475,499 B2 | 7/2013 | Cournoyer et al. |
| 8,480,712 B1 | 7/2013 | Samuel et al. |
| 8,518,086 B2 | 8/2013 | Seme et al. |
| 8,828,058 B2 | 9/2014 | Elsebaie et al. |
| 8,920,472 B2 | 12/2014 | Seme et al. |
| 9,333,009 B2 | 5/2016 | Kroll et al. |
| 2001/0037111 A1 | 11/2001 | Dixon et al. |
| 2002/0032442 A1 | 3/2002 | Altarac et al. |
| 2002/0133155 A1 | 9/2002 | Ferree |
| 2002/0143329 A1 | 10/2002 | Serhan et al. |
| 2002/0151978 A1 | 10/2002 | Zacouto et al. |
| 2003/0040746 A1 | 2/2003 | Mitchell et al. |
| 2003/0045878 A1 | 3/2003 | Petit et al. |
| 2003/0093117 A1 | 5/2003 | Saadat |
| 2003/0109881 A1 | 6/2003 | Shirado et al. |
| 2003/0114853 A1 | 6/2003 | Burgess et al. |
| 2003/0153915 A1 | 8/2003 | Nekozuka et al. |
| 2003/0220643 A1 | 11/2003 | Ferree |
| 2004/0006391 A1 | 1/2004 | Reiley |
| 2004/0049274 A1 | 3/2004 | Reiley |
| 2004/0049277 A1 | 3/2004 | Reiley |
| 2004/0097931 A1 | 5/2004 | Mitchell |
| 2004/0106921 A1 | 6/2004 | Cheung et al. |
| 2004/0149065 A1 | 8/2004 | Moran |
| 2004/0167520 A1 | 8/2004 | Zucherman et al. |
| 2004/0215190 A1 | 10/2004 | Nguyen et al. |
| 2004/0230201 A1 | 11/2004 | Yuan et al. |
| 2004/0230304 A1 | 11/2004 | Yuan et al. |
| 2005/0027361 A1 | 2/2005 | Reiley |
| 2005/0033291 A1 | 2/2005 | Ebara |
| 2005/0033295 A1 | 2/2005 | Wisnewski |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0080420 A1 | 4/2005 | Farris et al. |
| 2005/0080486 A1 | 4/2005 | Fallin et al. |
| 2005/0107789 A1 | 5/2005 | Sweeney |
| 2005/0113927 A1 | 5/2005 | Malek |
| 2005/0113928 A1 | 5/2005 | Cragg et al. |
| 2005/0131537 A1 | 6/2005 | Hoy et al. |
| 2005/0131538 A1 | 6/2005 | Chervitz et al. |
| 2005/0149030 A1 | 7/2005 | Serhan et al. |
| 2005/0154390 A1 | 7/2005 | Biedermann et al. |
| 2005/0165396 A1 | 7/2005 | Fortin et al. |
| 2005/0171538 A1 | 8/2005 | Sgier et al. |
| 2005/0177240 A1 | 8/2005 | Blain |
| 2005/0203509 A1 | 9/2005 | Chinnaian et al. |
| 2005/0203511 A1 | 9/2005 | Wilson-MacDonald et al. |
| 2005/0203514 A1 | 9/2005 | Jahng et al. |
| 2005/0203516 A1 | 9/2005 | Biedermann et al. |
| 2005/0209603 A1 | 9/2005 | Zucherman et al. |
| 2005/0216004 A1 | 9/2005 | Schwab |
| 2005/0228326 A1 | 10/2005 | Kalfas et al. |
| 2005/0228377 A1 | 10/2005 | Chao et al. |
| 2005/0234453 A1 | 10/2005 | Shaolian et al. |
| 2005/0240264 A1 | 10/2005 | Tokish et al. |
| 2005/0245929 A1 | 11/2005 | Winslow et al. |
| 2005/0261685 A1 | 11/2005 | Fortin et al. |
| 2005/0261770 A1 | 11/2005 | Kuiper et al. |
| 2005/0267470 A1 | 12/2005 | McBride |
| 2005/0267579 A1 | 12/2005 | Reiley et al. |
| 2006/0004449 A1 | 1/2006 | Goble et al. |
| 2006/0009767 A1 | 1/2006 | Kiester |
| 2006/0009847 A1 | 1/2006 | Reiley |
| 2006/0009849 A1 | 1/2006 | Reiley |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058790 A1 | 3/2006 | Carl et al. |
| 2006/0058791 A1 | 3/2006 | Broman et al. |
| 2006/0058792 A1 | 3/2006 | Hynes |
| 2006/0064091 A1 | 3/2006 | Ludwig et al. |
| 2006/0084976 A1 | 4/2006 | Borgstrom et al. |
| 2006/0084996 A1 | 4/2006 | Metz-Stavenhagen |
| 2006/0085075 A1 | 4/2006 | McLeer |
| 2006/0116686 A1 | 6/2006 | Crozet |
| 2006/0142758 A1 | 6/2006 | Petit |
| 2006/0142760 A1 | 6/2006 | McDonnell |
| 2006/0149234 A1 | 7/2006 | de Coninck |
| 2006/0189984 A1 | 8/2006 | Fallin et al. |
| 2006/0200149 A1 | 9/2006 | Hoy et al. |
| 2006/0212034 A1 | 9/2006 | Triplett et al. |
| 2006/0217712 A1 | 9/2006 | Mueller et al. |
| 2006/0217715 A1 | 9/2006 | Serhan et al. |
| 2006/0217718 A1 | 9/2006 | Chervitz et al. |
| 2006/0229616 A1 | 10/2006 | Albert et al. |
| 2006/0241594 A1 | 10/2006 | McCarthy et al. |
| 2006/0241598 A1 | 10/2006 | Khalili |
| 2006/0247627 A1 | 11/2006 | Farris |
| 2006/0253118 A1 | 11/2006 | Bailey |
| 2006/0271050 A1 | 11/2006 | Piza Vallespir |
| 2006/0276787 A1 | 12/2006 | Zubok et al. |
| 2006/0293663 A1 | 12/2006 | Walkenhorst et al. |
| 2007/0005062 A1 | 1/2007 | Lange et al. |
| 2007/0016296 A1 | 1/2007 | Triplett et al. |
| 2007/0055373 A1 | 3/2007 | Hudgins et al. |
| 2007/0073293 A1 | 3/2007 | Martz et al. |
| 2007/0079517 A1 | 4/2007 | Augostino et al. |
| 2007/0083200 A1 | 4/2007 | Gittings et al. |
| 2007/0093814 A1 | 4/2007 | Callahan et al. |
| 2007/0093833 A1 | 4/2007 | Kuiper et al. |
| 2007/0161987 A1 | 7/2007 | Capote et al. |
| 2007/0161993 A1 | 7/2007 | Lowery et al. |
| 2007/0161994 A1 | 7/2007 | Lowery et al. |
| 2007/0162002 A1 | 7/2007 | Tornier |
| 2007/0167946 A1 | 7/2007 | Triplett et al. |
| 2007/0167947 A1 | 7/2007 | Gittings |
| 2007/0168035 A1 | 7/2007 | Koske |
| 2007/0185492 A1 | 8/2007 | Chervitz et al. |
| 2007/0191846 A1 | 8/2007 | Bruneau et al. |
| 2007/0198014 A1 | 8/2007 | Graf et al. |
| 2007/0213716 A1 | 9/2007 | Lenke et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0233075 A1 | 10/2007 | Dawson |
| 2007/0233090 A1 | 10/2007 | Naifeh et al. |
| 2007/0233093 A1 | 10/2007 | Falahee |
| 2007/0238335 A1 | 10/2007 | Veldman et al. |
| 2007/0270803 A1 | 11/2007 | Giger et al. |

(56) References Cited

U.S. PATENT DOCUMENTS

| | | |
|---|---|---|
| 2007/0270805 A1 | 11/2007 | Miller et al. |
| 2007/0270817 A1 | 11/2007 | Rezach |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270967 A1 | 11/2007 | Fallin et al. |
| 2007/0276374 A1 | 11/2007 | Broman et al. |
| 2007/0288011 A1 | 12/2007 | Logan |
| 2007/0288024 A1 | 12/2007 | Gollogly |
| 2008/0015577 A1 | 1/2008 | Loeb |
| 2008/0021466 A1 | 1/2008 | Shadduck et al. |
| 2008/0021469 A1 | 1/2008 | Holt |
| 2008/0027436 A1 | 1/2008 | Cournoyer et al. |
| 2008/0033436 A1 | 2/2008 | Song et al. |
| 2008/0045954 A1 | 2/2008 | Reiley et al. |
| 2008/0065069 A1 | 3/2008 | Betz et al. |
| 2008/0077143 A1 | 3/2008 | Shluzas |
| 2008/0086213 A1 | 4/2008 | Reiley |
| 2008/0091202 A1 | 4/2008 | Reiley |
| 2008/0091210 A1 | 4/2008 | Reiley |
| 2008/0091268 A1 | 4/2008 | Reiley |
| 2008/0097437 A1 | 4/2008 | Reiley |
| 2008/0097438 A1 | 4/2008 | Reiley |
| 2008/0097439 A1 | 4/2008 | Reiley |
| 2008/0097440 A1 | 4/2008 | Reiley et al. |
| 2008/0097441 A1 | 4/2008 | Hayes et al. |
| 2008/0097446 A1 | 4/2008 | Reiley et al. |
| 2008/0097609 A1 | 4/2008 | Reiley |
| 2008/0097612 A1 | 4/2008 | Reiley |
| 2008/0097613 A1 | 4/2008 | Reiley et al. |
| 2008/0132951 A1 | 6/2008 | Reiley et al. |
| 2008/0140202 A1 | 6/2008 | Allard et al. |
| 2008/0167688 A1 | 7/2008 | Fauth et al. |
| 2008/0177326 A1 | 7/2008 | Thompson |
| 2008/0183209 A1 | 7/2008 | Robinson et al. |
| 2008/0183212 A1 | 7/2008 | Veldman et al. |
| 2008/0195100 A1 | 8/2008 | Capote et al. |
| 2008/0195153 A1 | 8/2008 | Thompson |
| 2008/0195154 A1 | 8/2008 | Brown et al. |
| 2008/0200953 A1 | 8/2008 | Reiley et al. |
| 2008/0221622 A1 | 9/2008 | Triplett et al. |
| 2008/0228227 A1 | 9/2008 | Brown et al. |
| 2008/0234737 A1 | 9/2008 | Boschert |
| 2008/0234739 A1 | 9/2008 | Hudgins et al. |
| 2008/0262546 A1 | 10/2008 | Calvosa et al. |
| 2008/0269805 A1 | 10/2008 | Dekutoski et al. |
| 2008/0275507 A1 | 11/2008 | Triplett et al. |
| 2008/0292161 A1 | 11/2008 | Funk et al. |
| 2008/0306535 A1 | 12/2008 | Winslow et al. |
| 2008/0306536 A1 | 12/2008 | Frigg et al. |
| 2008/0319483 A1 | 12/2008 | Triplett et al. |
| 2008/0319484 A1 | 12/2008 | Fauth |
| 2008/0319485 A1 | 12/2008 | Fauth et al. |
| 2008/0319488 A1 | 12/2008 | Helgerson |
| 2008/0319489 A1 | 12/2008 | Triplett |
| 2009/0012565 A1 | 1/2009 | Sachs et al. |
| 2009/0012566 A1 | 1/2009 | Fauth |
| 2009/0018583 A1 | 1/2009 | Song et al. |
| 2009/0024134 A1 | 1/2009 | Triplett et al. |
| 2009/0024135 A1 | 1/2009 | Triplett et al. |
| 2009/0024166 A1 | 1/2009 | Carl et al. |
| 2009/0024167 A1 | 1/2009 | Chervitz et al. |
| 2009/0024168 A1 | 1/2009 | Chervitz et al. |
| 2009/0024169 A1 | 1/2009 | Triplett et al. |
| 2009/0030459 A1 | 1/2009 | Hoy et al. |
| 2009/0030460 A1 | 1/2009 | Chervitz et al. |
| 2009/0030461 A1 | 1/2009 | Hoy et al. |
| 2009/0036929 A1 | 2/2009 | Reglos et al. |
| 2009/0048632 A1 | 2/2009 | Firkins et al. |
| 2009/0062864 A1 | 3/2009 | Ludwig et al. |
| 2009/0062915 A1 | 3/2009 | Kohm et al. |
| 2009/0069849 A1 | 3/2009 | Oh et al. |
| 2009/0082871 A1 | 3/2009 | Fallin et al. |
| 2009/0088802 A1 | 4/2009 | Fallin |
| 2009/0093820 A1 | 4/2009 | Trieu et al. |
| 2009/0099607 A1 | 4/2009 | Fallin et al. |
| 2009/0112207 A1 | 4/2009 | Walker et al. |
| 2009/0112262 A1 | 4/2009 | Pool et al. |
| 2009/0112263 A1 | 4/2009 | Pool et al. |
| 2009/0125062 A1 | 5/2009 | Arnin |
| 2009/0194206 A1 | 8/2009 | Jeon et al. |
| 2009/0204156 A1 | 8/2009 | McClintock et al. |
| 2009/0259256 A1 | 10/2009 | Miller |
| 2009/0281575 A1 | 11/2009 | Carls et al. |
| 2010/0057129 A1 | 3/2010 | Goble et al. |
| 2010/0076493 A1 | 3/2010 | Fauth et al. |
| 2010/0082107 A1 | 4/2010 | Fauth et al. |
| 2010/0087880 A1 | 4/2010 | Fauth et al. |
| 2010/0100130 A1 | 4/2010 | Carl et al. |
| 2010/0100133 A1 | 4/2010 | Carl et al. |
| 2010/0106192 A1 | 4/2010 | Barry |
| 2010/0137913 A1 | 6/2010 | Khatchadourian et al. |
| 2010/0249836 A1 | 9/2010 | Seme |
| 2010/0249837 A1 | 9/2010 | Seme et al. |
| 2010/0256684 A1 | 10/2010 | Seme et al. |
| 2010/0274286 A1 | 10/2010 | Blain et al. |
| 2010/0286730 A1 | 11/2010 | Gordon |
| 2010/0318129 A1 | 12/2010 | Seme et al. |
| 2011/0054536 A1 | 3/2011 | Elsebaie et al. |
| 2011/0060367 A1 | 3/2011 | Stauber |
| 2011/0066188 A1 | 3/2011 | Seme et al. |
| 2011/0245876 A1 | 10/2011 | Brumfield |
| 2011/0301645 A1 | 12/2011 | Connor |
| 2012/0109197 A1 | 5/2012 | Carl et al. |
| 2012/0221057 A1 | 8/2012 | Zhang et al. |
| 2012/0255380 A1 | 10/2012 | Wu |
| 2013/0066426 A1 | 3/2013 | Martinson et al. |
| 2013/0123851 A1 | 5/2013 | Seme et al. |
| 2013/0123853 A1 | 5/2013 | Seme et al. |
| 2013/0184757 A1 | 7/2013 | Seme et al. |
| 2013/0211455 A1 | 8/2013 | Seme |
| 2013/0231703 A1 | 9/2013 | Seme et al. |
| 2014/0236234 A1 | 8/2014 | Kroll et al. |
| 2014/0350602 A1 | 11/2014 | Seme et al. |

FOREIGN PATENT DOCUMENTS

| | | |
|---|---|---|
| EP | 0260044 A1 | 3/1988 |
| EP | 0322334 A1 | 6/1989 |
| EP | 0418387 A1 | 3/1991 |
| EP | 1281361 A1 | 2/2003 |
| FR | 2697744 A1 | 5/1994 |
| FR | 2736535 A1 | 1/1997 |
| FR | 2781359 A1 | 1/2000 |
| FR | 2801492 A1 | 6/2001 |
| FR | 2872021 A1 | 12/2005 |
| FR | 2900563 A1 | 11/2007 |
| GB | 780652 A | 8/1957 |
| SU | 888968 A1 | 12/1981 |
| WO | 9213496 A1 | 8/1992 |
| WO | 2004017705 A2 | 3/2004 |
| WO | 2006010844 A1 | 2/2006 |
| WO | 2006017641 A2 | 2/2006 |
| WO | 2006136937 A2 | 12/2006 |
| WO | 2007051924 A1 | 5/2007 |
| WO | 2008086467 A2 | 7/2008 |
| WO | 2008154313 A1 | 12/2008 |
| WO | 2010053662 A1 | 5/2010 |
| WO | 2010056650 A1 | 5/2010 |
| WO | 2010111500 A2 | 9/2010 |
| WO | 2014172632 A2 | 10/2014 |

OTHER PUBLICATIONS

Chinese Office Action dated Aug. 25, 2015, issued in Chinese Application No. 2012800383489.

Berry, James L. et al., A Morphometric Study of Human Lumbar and Selected Thoracic Vertebrae, 12 Spine 362 (1987).

Eglin, D. et al., "Degradable Polymeric Materials for Osteosynthesis: tutorial", European Cells and Materials, vol. 16, 2008, pp. 80-91.

European Search Report issued in EP Application No. 12154799, dated Mar. 2, 2012, 9 pages.

(56) References Cited

OTHER PUBLICATIONS

Fujita, Masaru et al., A Biomechanical Analysis of Sublaminar and Subtransverse Process Fixation Using Metal Wires and Polyethylene Cables, 31 Spine 2202 (2006).
Girardi, Federico P. et al., Safety of Sublaminar Wires With Isola Instrumentation for the Treatment of Idiopathic Scoliosis, 25 SPINE 691 (2000).
International Application No. PCT/US2008/065979, filed Jun. 5, 2008, entitled Medical Device and Method to Correct Deformity.
International Application No. PCT/US2009/063833, filed Nov. 10, 2009, entitled Growth Directed Vertebral Fixation System With Distractible Connector(s) and Apical Control.
International Application No. PCT/US2010/028684, filed Mar. 25, 2010, entitled Semi-Constrained Anchoring System.
International Search Report and Written Opinion issued in PCT/US2005/027692, dated May 19, 2008, 4 pages.
International Search Report and Written Opinion issued in PCT/US2008/065979, dated Oct. 2, 2008, 7 pages.
International Search Report and Written Opinion issued in PCT/US2009/063833, dated Mar. 15, 2010, 14 pages.
International Search Report and Written Opinion issued in PCT/US2010/028684, dated Sep. 28, 2010, 19 pages.
International Search Report and Written Opinion issued in PCT/US2010/036375, dated Sep. 10, 2010, 16 pages.
International Search Report and Written Opinion issued in PCT/US2010/047117, dated Dec. 2, 2010.
International Search Report and Written Opinion issued in PCT/US2011/049693, dated Nov. 15, 2011, 16 pages.
International Search Report and Written Opinion issued in PCT/US2012/040493, dated Aug. 21, 2012, 15 pages.
International Search Report and Written Opinion issued in PCT/US2012/065262, dated Feb. 5, 2013, 8 pages.
International Search Report and Written Opinion issued in PCT/US2013/065488, dated Feb. 18, 2014, 10 pages.
Invitation to Pay Additional Fees and Partial Search Report issued in PCT/US2010/028684, dated Jun. 30, 2010, 6 pages.
Liljenqvist, Ulf R. et al., Analysis of Vertebral Morphology in Idiopathic Scoliosis with Use of Magnetic Resonance Imaging and Multiplanar Reconstruction, 84 J Bone Joint Surg Am. 359 (2002).
Molnar, Szabolcs et al., Ex Vivo and in Vitro Determination of the Axial Rotational Axis of the Human Thoracic Spine, 31 Spine E984 (2006).
Rajasekaran, S. et al., Eighteen-Level Analysis of Vertebral Rotation Following Harrington-Luque Instrumentation in Idiopathic Scoliosis, 76 J Bone Joint Surg Am. 104 (1994).
Wenger, Dennis R. et al., Biomechanics of Scoliosis Correction by Segmental Spinal Instrumentation, 7 Spine 260 (1982).
White III, Augustus A. et al., Biomechancis of the Spine 28-29, Tbl. 1-5 (2d ed. 1990).

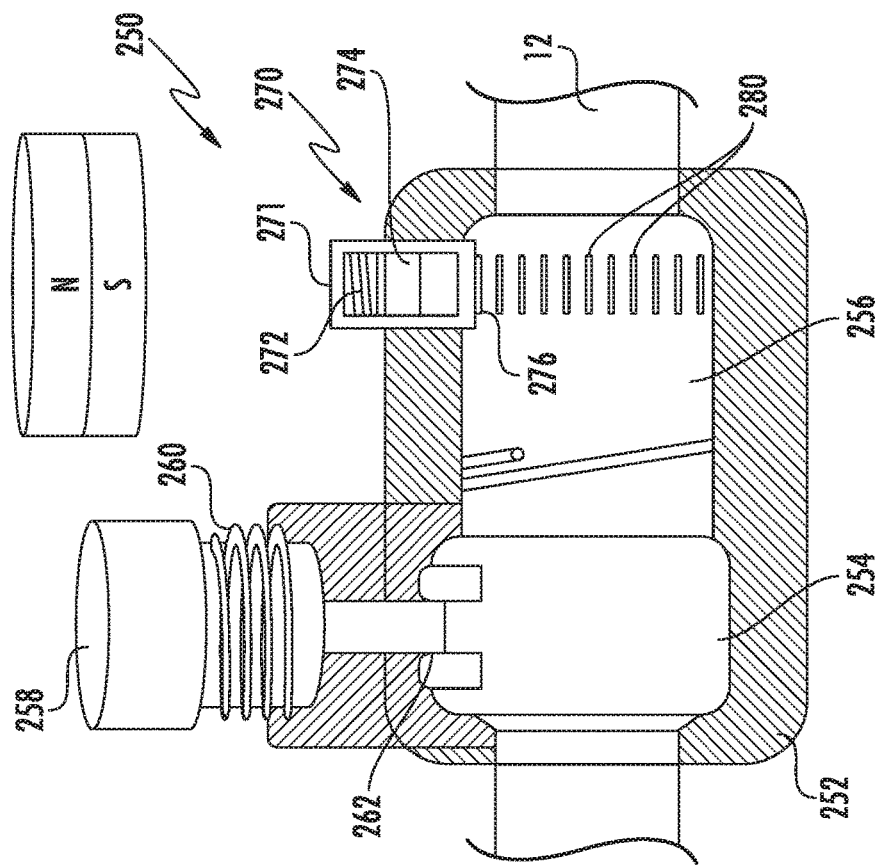
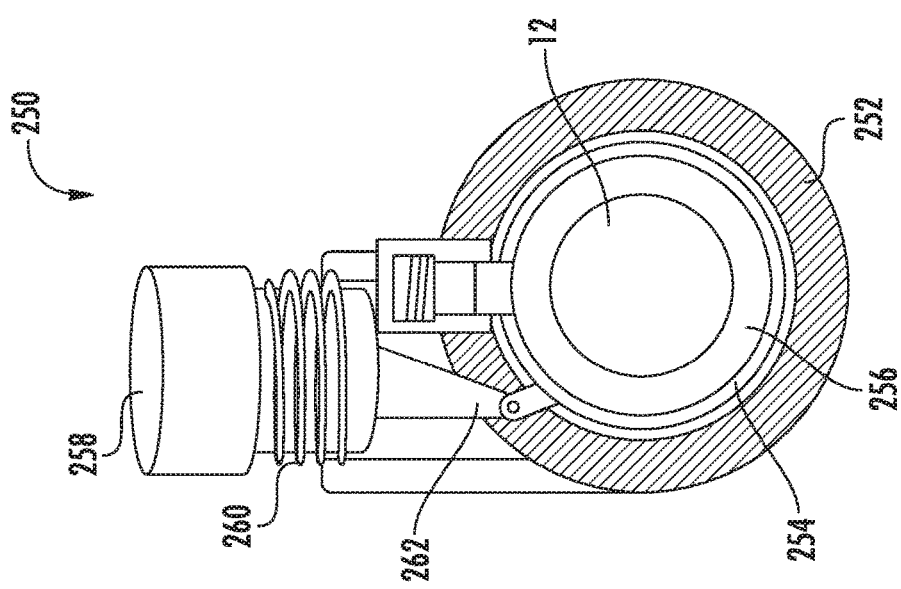

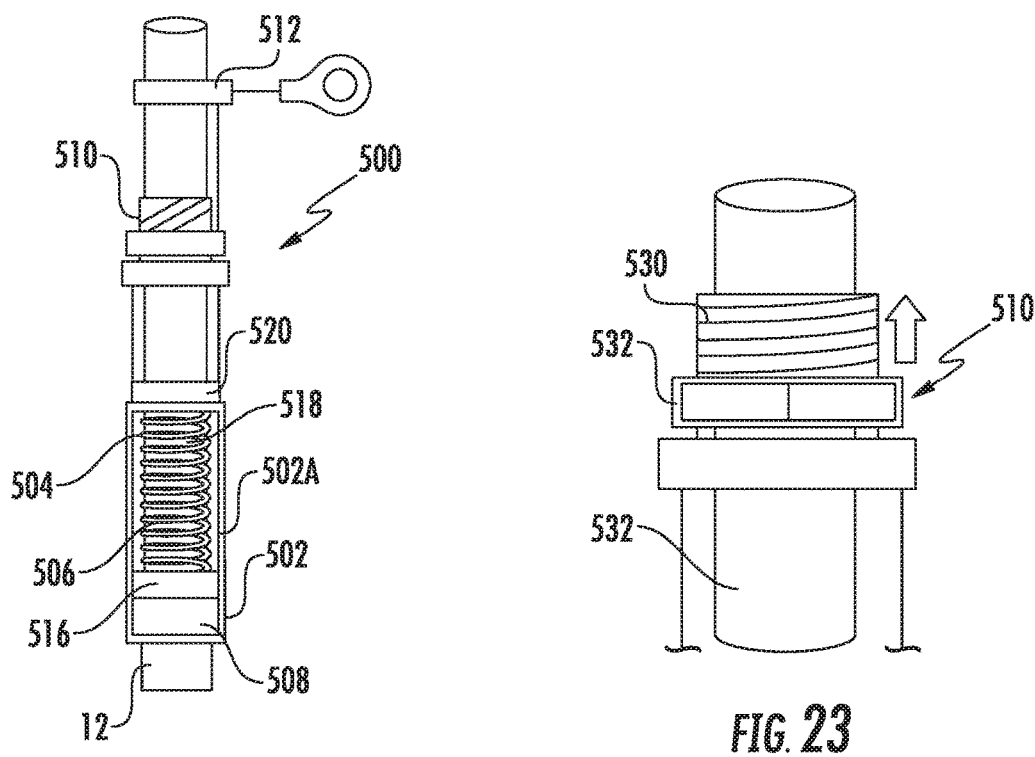
FIG. 22
FIG. 23
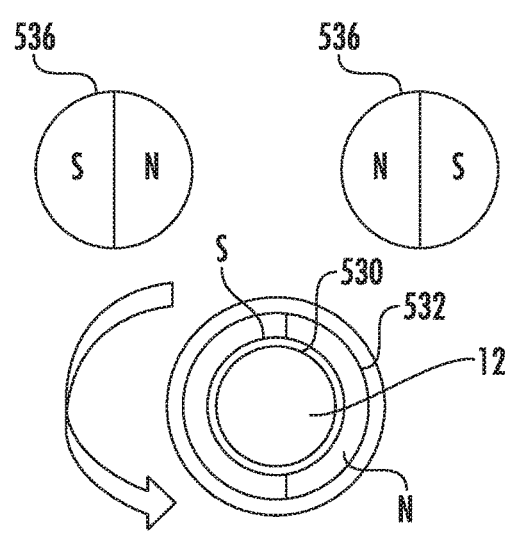
FIG. 24

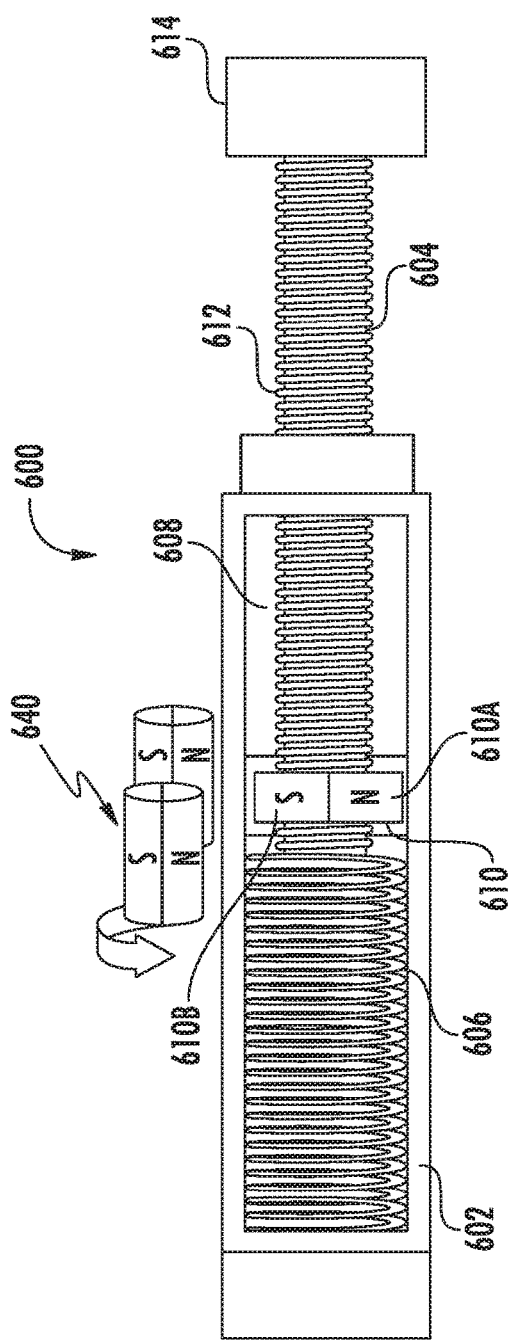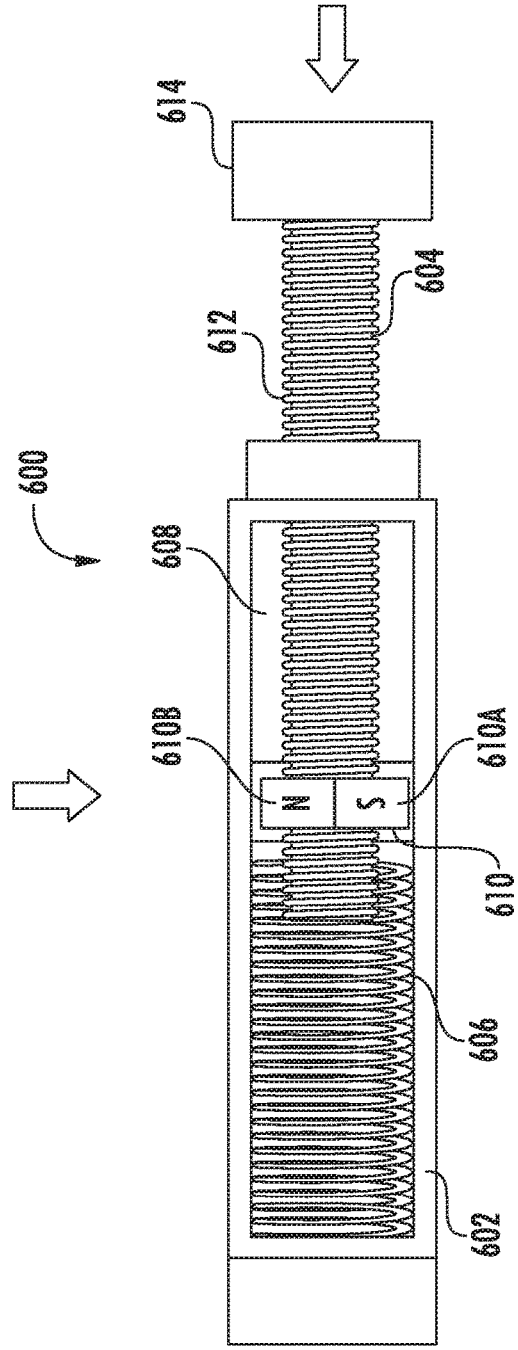

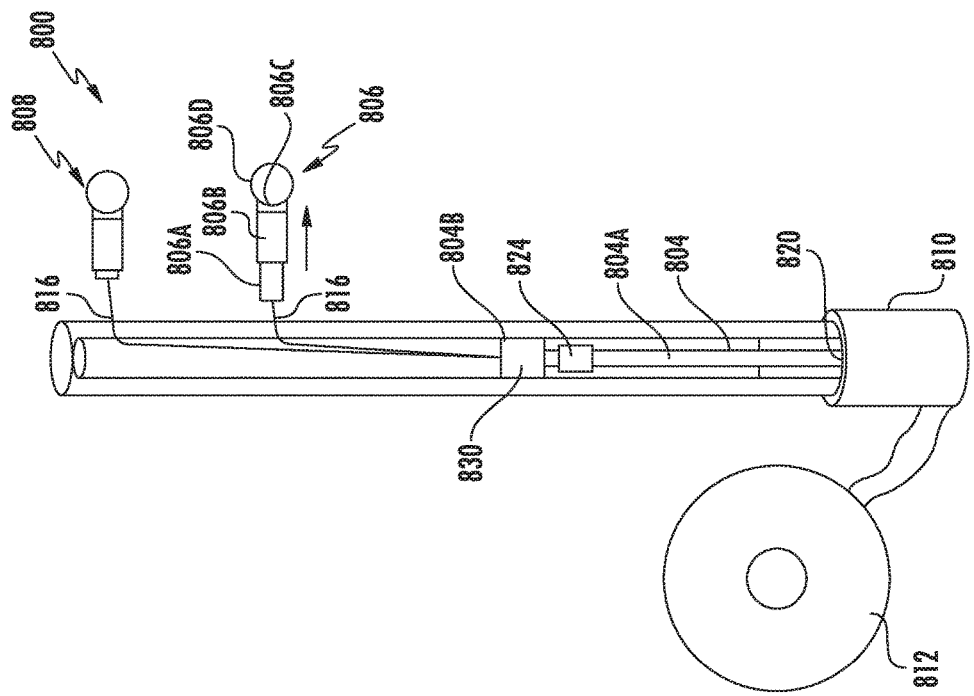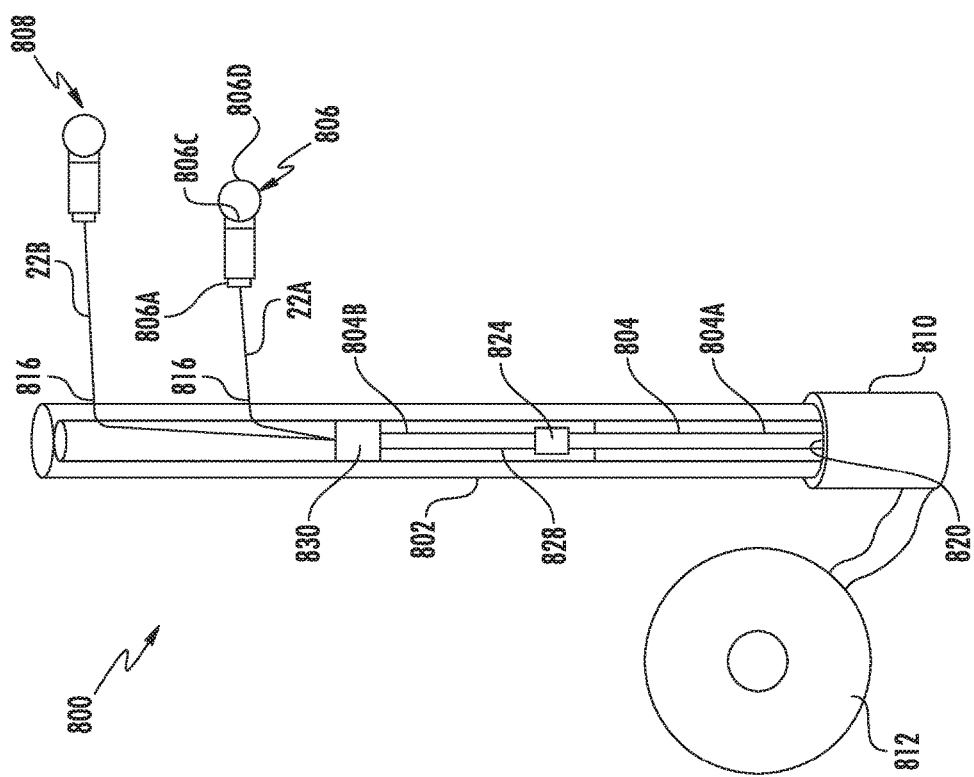

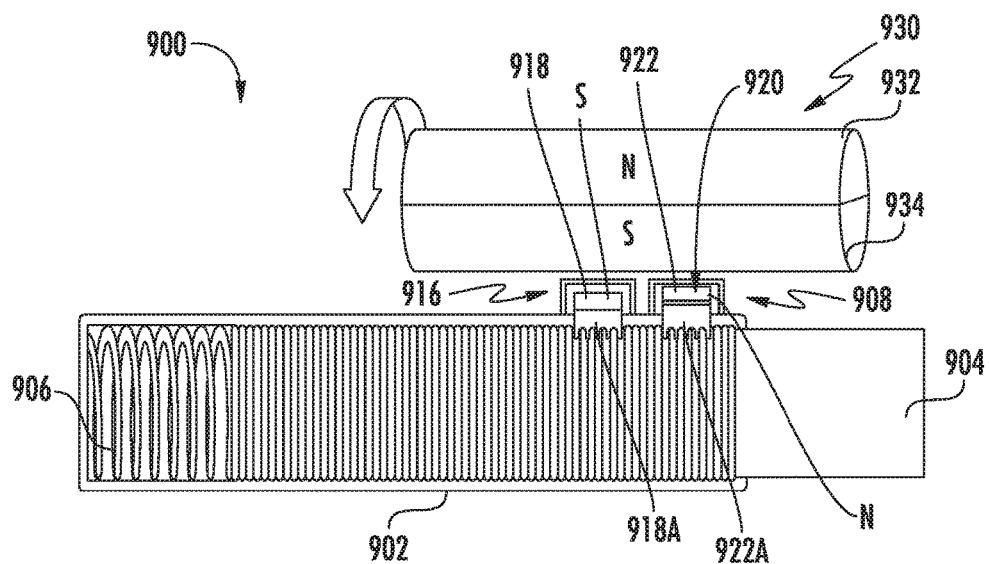
FIG. 39
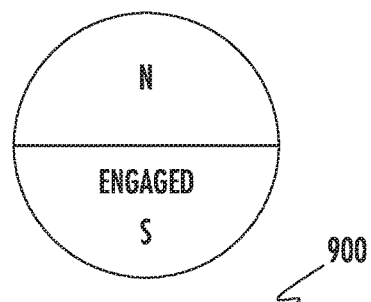
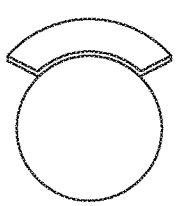
FIG. 40
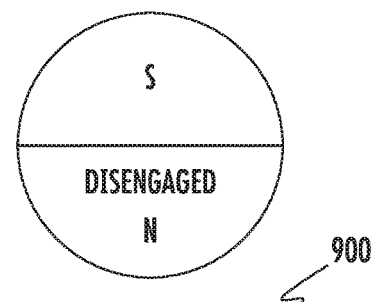
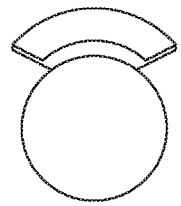
FIG. 41

SPINAL CORRECTION SYSTEM ACTUATORS

CROSS-REFERENCE TO RELATED APPLICATIONS

This application is a continuation of U.S. application Ser. No. 14/123,729, filed on May 1, 2014 and entitled "SPINAL CORRECTION SYSTEM ACTUATORS", which is a U.S. National Stage Application filed under 35 U.S.C. § 371(a) of International Application Serial No. PCT/US12/040439, internationally filed Jun. 1, 2012 and entitled "SPINAL CORRECTION SYSTEM ACTUATORS", which claims priority to U.S. Provisional Application No. 61/493,117, filed on Jun. 3, 2011 and entitled "SPINAL CORRECTION SYSTEM ACTUATORS", the entire contents of each of the above applications are incorporated herein by reference for all purposes.

BACKGROUND

Many systems have been utilized to treat spinal deformities such as scoliosis, spondylolisthesis, and a variety of others. Primary surgical methods for correcting a spinal deformity utilize instrumentation to correct the deformity as much as possible, as well as implantable hardware systems to rigidly stabilize and maintain the correction. Many of these implantable hardware systems rigidly fix the spinal column or allow limited growth and/or other movement of the spinal column, to help facilitate fusion after the column has been moved to a corrected position.

SUMMARY

Some inventive aspects relate to a spinal correction system for implantation in a patient, the system including a reciprocating adjuster and/or a resistance adjuster coupled to a stabilizing member, for example. In some embodiments, the resistance adjuster includes a potential energy drive, a slide unit, a and a resistance unit. In some embodiments, the reciprocating adjuster includes a piston unit, a transfer unit coupled to the piston unit, and a return mechanism.

BRIEF DESCRIPTION OF THE DRAWINGS

FIGS. 11 and 12 show another tensioning system that is optionally employed in addition to, or as a replacement for, one or more of the tensioners, according to some embodiments.

FIGS. 22, 23 and 24 show another tensioning system that is optionally employed in addition to, or as a replacement for, one or more of the tensioners, according to some embodiments.

FIGS. 27 and 28 show an expanding stabilizing member system that is optionally employed in addition to, or as a replacement for, the stabilizing member of the system of FIG. 1, according to some embodiments.

FIG. 30 shows the first actuator collar in a free spinning, or unlocked state, and FIG. 31 shows the first actuator collar in a locked, or engaged state, according to some embodiments.

FIGS. 35 and 36 show another tensioning system that is optionally employed in addition to, or as a replacement for, one or more of the tensioners, according to some embodiments.

FIGS. 39, 40, and 41 show an expanding stabilizing member system that is optionally employed in addition to, or as a replacement for, the stabilizing member of the system of FIG. 1, according to some embodiments.

Figure 1:
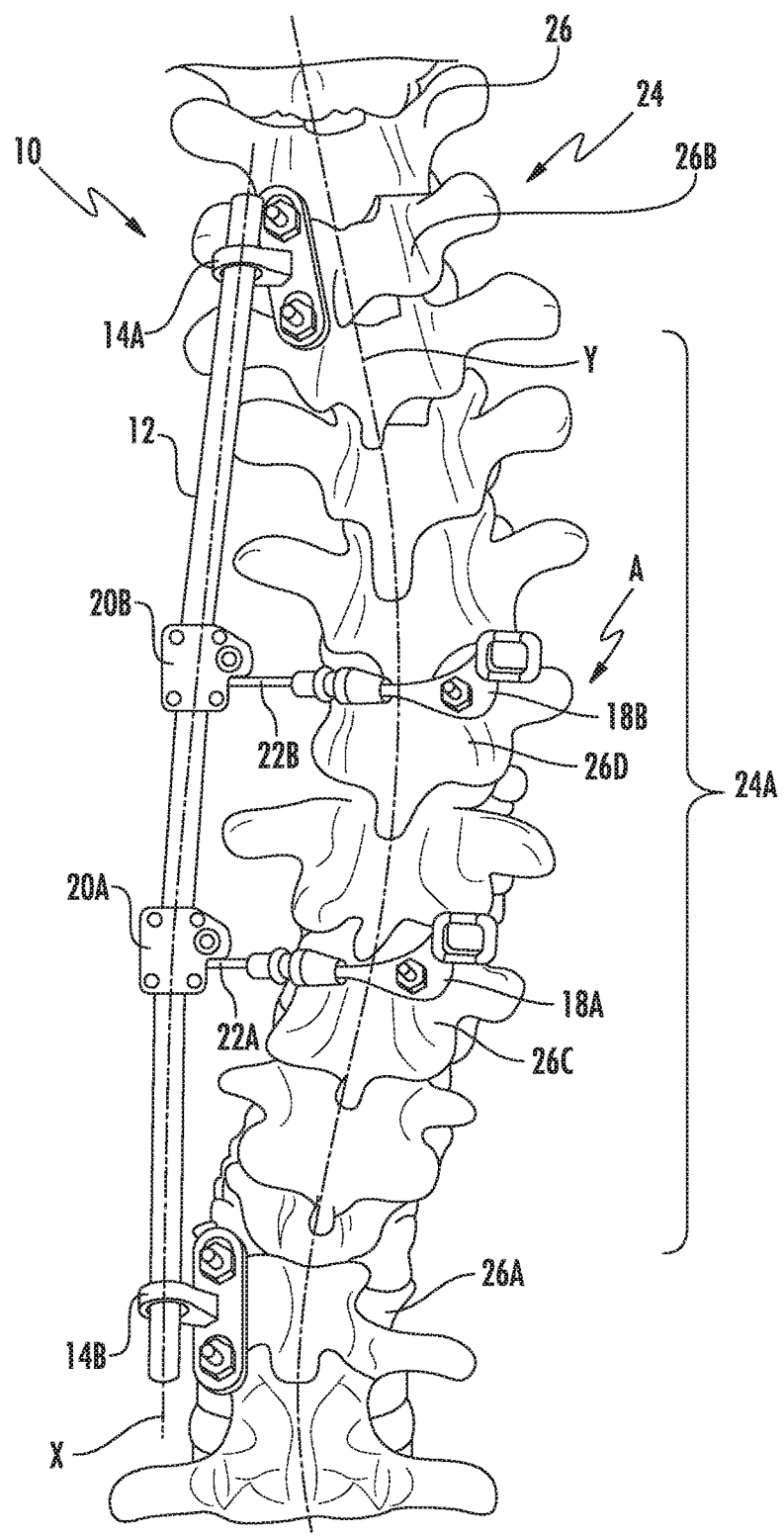
FIG. 1 shows a system for correcting a spine tending to exhibit a spinal deformity, according to some embodiments.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

Some embodiments relate to a system for correcting spinal deformities, as well as associated methods and devices. In general terms, the system provides lateral translational corrective force(s) and/or derotational corrective force(s) on a spinal column tending to exhibit a defective curvature. In some embodiments, the system facilitates incremental correction, gross correction, and/or correction maintenance as desired.

Various planes and associated directions are referenced in the following description, including a sagittal plane defined by two axes, one drawn between a head (superior) and tail (inferior) of the body and one drawn between a back (posterior) and front (anterior) of the body; a coronal plane defined by two axes, one drawn between a center (medial) to side (lateral) of the body and one drawn between the head and tail of the body; and a transverse plane defined by two axes, one drawn between a back and front of the body and one drawn between a center and side of the body.

Also, the terms pitch, roll, and yaw are used, where roll generally refers to angulation, or rotation, in a first plane through which a longitudinal axis of a body orthogonally passes (e.g., rotation about a longitudinal axis corresponding to the spinal column), pitch refers to angulation, or rotation, in a second plane orthogonal to the first plane, and yaw refers to angulation, or rotation, in a third plane orthogonal to the first and second planes. In some embodiments, pitch is angulation in the sagittal plane, yaw is angulation in the coronal plane, and roll is angulation in the transverse plane. In various embodiments, changes in pitch, yaw, and/or roll occur concurrently or separately as desired. Moreover, as used herein, "lateral translation" is not limited to translation along the medial-lateral axis (in either the lateral-medial or medial-lateral direction(s)) unless specified as such.

FIG. 1 is a perspective view of a system 10 for correcting a spine tending to exhibit a spinal deformity, according to some embodiments. As shown in FIG. 1, the system 10 includes a stabilizing member 12; a plurality of stabilizing anchors 14, including a first stabilizing anchor 14A and a second stabilizing anchor 14B; a plurality of correction anchors 18 including a first correction anchor 18A and a second correction anchor 18B; a plurality of tensioners 20 including a first tensioner 20A and a second tensioner 20B; and a plurality of connectors 22 including a first connector 22A and a second connector 22B. As shown, the system 10 is secured to a spinal column 24 formed of a plurality of vertebrae 26, including a first vertebra 26A, a second vertebra 26B, a third vertebra 26C, and a fourth vertebra 26D.

In some embodiments, the stabilizing member 12 is also referred to as a rod or alignment member; the stabilizing anchors 14 are also referred to as alignment supports or guides; the correction anchors 18 are also referred to as anchor arms or vertebral levers, the tensioners 20 are also referred to as adjustment mechanisms or tying devices, and the connectors 22 are also referred to as force directing members or cables, for example. Although the system 10 is shown with two stabilizing anchors 14, two correction anchors 18, two tensioners 20, and two connectors 22, a greater or fewer number thereof are implemented as appropriate. As described in greater detail below, the tensioners 20 and/or stabilizing member 12 are optionally replaced and/or augmented by a variety of other tensioning and expanding stabilizing member systems.

Some examples of suitable stabilizing members 12, stabilizing anchors 14, correction anchors 18, tensioners 20, and/or connectors 22 according to some embodiments are described in U.S. application Ser. No. 12/411,562, filed Mar. 26, 2009, and entitled "Semi-Constrained Anchoring System"; U.S. application Ser. No. 11/196,952, filed Aug. 3, 2005, and entitled "Device and Method for Correcting a Spinal Deformity"; and U.S. application Ser. No. 12/134,058, filed Jun. 5, 2008, and entitled "Medical Device and Method to Correct Deformity," the entire contents of each which are incorporated herein by reference for all purposes.

As shown, the spinal column 24 has a transverse centerline of rotation Y, also described as a longitudinal axis of rotation. In some embodiments, the transverse centerline rotation Y of the spinal column 24 generally corresponds to a mid-distance position of the spinal canal (not shown) extending through the spinal column 24, where each vertebra 26 has a transverse center of rotation generally located on the transverse centerline of rotation Y.

As shown in FIG. 1, the correction anchors 18 are fixed to a target region 24A of the spinal column 24 tending to exhibit an abnormal, or defective curvature (e.g., scoliosis) in need of correction. The system 10 is optionally used to apply derotational and/or lateral translational forces on the target region 24A of the spinal column 24 to translate and/or maintain the spinal column 24 at a desired curvature.

In some embodiments, the stabilizing member 12 is substantially elongate and rigid, and, if desired, the stabilizing member 12 incorporates some flex, or springiness while substantially rigidly retaining its shape. As will be described in greater detail, the stabilizing member 12 is adapted, or otherwise structured, to extend along the spinal column 24 at a desired spacing from the vertebrae 26 of the spinal column 24. In some embodiments, the stabilizing member 12 is partially or fully contoured to a typical, corrected curvature of the spinal column 24. The stabilizing member 12 has a longitudinal axis X and where the stabilizing member 12 is substantially straight, the longitudinal axis X is substantially straight. Where the stabilizing member 12 has curved or angled portions, the longitudinal axis X at those portions is similarly curved or angled. As described in greater detail, the stabilizing member 12 optionally includes features for adjusting a length of the stabilizing member 12.

FIG. 1 shows the pair of stabilizing anchors 14A, 14B which are adapted, or otherwise structured, to be mounted or fixed to one or more stabilizing vertebrae, such as the first and second vertebrae 26A, 26B. The first and second stabilizing anchors 14A, 14B are further adapted to receive, and include means for receiving, the stabilizing member 12 such that the stabilizing member 12 is secured laterally, against lateral translation relative to the first and second stabilizing anchors 14A, 14B.

In some embodiments, the stabilizing anchors 14 are secured to a single one of the vertebra 26 (e.g., laterally across the vertebra at the pedicles, or at a single point, such as a single pedicle). The first and second stabilizing anchors 14A, 14B are each secured to a single vertebra in some embodiments or multiple vertebrae in others, such as an additional, adjacent one of the vertebra 26. As shown in FIG.

1, the first and second stabilizing anchors 14A, 14B are secured to the first and second vertebrae 26A, 26B, respectively, as well as one of the vertebrae 26 adjacent each of the first and second vertebrae 26A, 26B. As received by the first and second stabilizing anchors 14A, 14B, the stabilizing member 12 is semi-constrained by the stabilizing anchors 14, the stabilizing member 12 being free to move with natural movements of the spinal column 24 while being substantially prevented from translating in a direction that is substantially perpendicular to the longitudinal axis X of the stabilizing member 12 at each of the stabilizing anchors 14A, 14B.

In some embodiments, the stabilizing member 12 is able to slide axially, or translate axially in one or two directions, along the longitudinal axis X, relative to the first and/or second stabilizing anchors 14A, 14B. The stabilizing member 12 is able to slide and to change in at least pitch and yaw at the first and second stabilizing anchors 14A, 14B. If desired, the stabilizing member 12 is also able to change in roll at the first and/or the second stabilizing anchors 14A, 14B. Thus, in some embodiments, the stabilizing anchors 14 are adapted to receive the stabilizing member 12 and secure the stabilizing member 12 against substantial lateral translation relative to stabilizing vertebrae (e.g., the first and second vertebrae 26A, 26B). For example, the vertebrae 26A, 26B (as well as secondary vertebra to which the stabilizing anchors 14 are secured) are used to stabilize the stabilizing member 12 which defines a line of reference from which to adjust defective curvature by providing a series of anchor points toward which the target region 24A is able to be pulled.

The first and second correction anchors 18A, 18B are optionally substantially similar, and thus various features of the second correction anchor 18B are described in association with the first correction anchor 18A. Features of the first correction anchor 18A are designated with reference numbers followed by an "A" and similar features of the second correction anchor 18B are designated with similar reference numbers followed by a "B."

Figure 2:
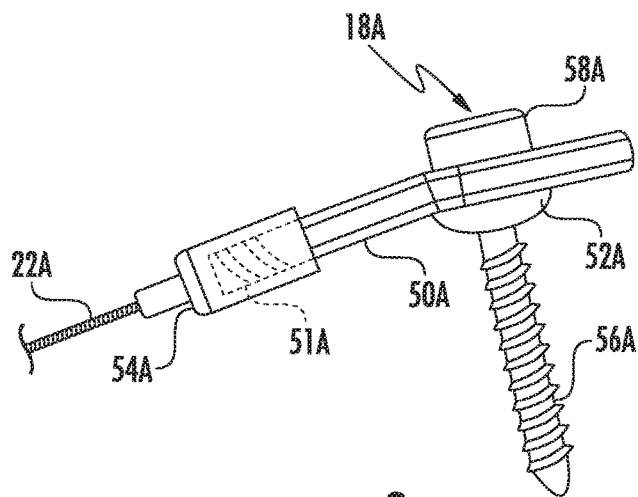
FIG. 2 shows a correction anchor and connector of the system of FIG. 1, according to some embodiments.

FIG. 2 shows the first correction anchor 18A according to some embodiments. As shown, the first correction anchor 18A is generally L-shaped, where the first correction anchor 18A includes an arm 50A with optional threading 51A (shown in broken lines) and a head 52A assembled to one another in a generally L-shaped configuration. The first correction anchor 18A is optionally substantially rigid. In some embodiments, the arm 50A extends from the head 52A to a terminal coupler 54A and is disposed generally perpendicular to the head 52A. In some embodiments, a length of the correction anchor 18A is adjustable, as described in greater detail below. The arm 50A is optionally secured about, and rotatable relative to the head 52A and is adapted to extend across one of the vertebrae 26, for example, from one side of the spinal column 24 to an opposite side of the spinal column 24.

The head 52A of the correction anchor 18A is optionally adapted or otherwise structured to be fixed to a portion of the third vertebra 26C, such as a pedicle of the third vertebra 26C. The head 52A includes a body portion 56A and a cap portion 58A. The head 52A includes and/or is adapted to work in conjunction with any of a variety of means for securing to the third vertebra 26C. For example, the body portion 56A is optionally configured as a pedicle screw. Assembly of the first correction anchor 18A includes receiving the arm 50A on the body portion 56A of the head 52A and screwing or otherwise securing the cap portion 58A onto the body portion 56A. In some embodiments, the arm 50A is rotatable relative to the head 52A upon assembly of the correction anchor 18A.

The first correction anchor 18A is secured to the third vertebra 26C such that the arm 50A extends across the third vertebra 26C either adjacent to the spinous processes or through a hole or hollowed portion in the spinous processes of the third vertebra 26C. In some embodiments, the second correction anchor 18B is secured to the fourth vertebra 26D, where the fourth vertebra 26D is an apical vertebra at the apex A of the target region 24A (FIG. 1).

Figure 3:
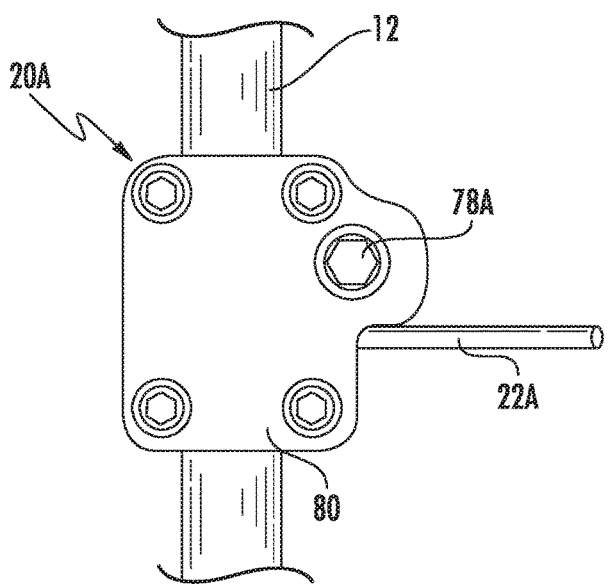
FIG. 3 shows a top view of a tensioner and a stabilizing member of the system of FIG. 1, according to some embodiments.
Figure 4:
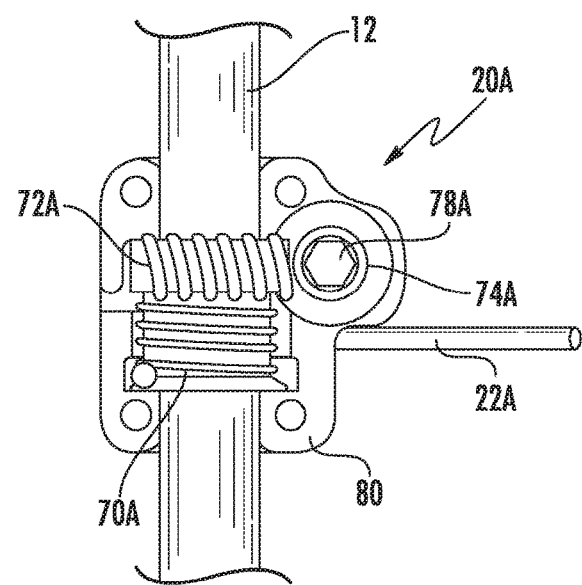
FIG. 4 shows the tensioner of FIG. 3 with a portion of a housing of the tensioner removed, according to some embodiments.

The first tensioner 20A is shown in FIGS. 3 and 4, where FIG. 4 shows the first tensioner 20A with a portion removed to illustrate inner features thereof. The tensioners 20 are optionally substantially similar, and thus various features of the first, and second tensioners 20A, 20B are described in association with the first tensioner 20A. Features of the first tensioner 20A are designated with reference numbers followed by an "A" and similar features of the second tensioner 20B are designated with similar reference numbers followed by a "B."

Generally, the first tensioner 20A provides means for securing the first connector 22A to the stabilizing member 12. In some embodiments, the first tensioner 20A, also described as an adjustment mechanism or coupler, is further adapted to adjust, and provides means for adjusting the effective length of the first connector 22A.

In some embodiments, the first tensioner 20A includes a reel 70A having a central lumen adapted to be coaxially received over the stabilizing member 12, a circumferential gear 72A surrounding the reel 70A, a vertical gear 74A in contact with the circumferential gear 72A, an actuation head 78A, and a housing 80A.

The reel 70A, as well as the circumferential gear 72A and vertical gear 74A are maintained at least partially within the housing 80A. In turn, the housing 80A is adapted to be secured to the stabilizing member 12. For example, the housing 80A optionally forms a clamshell configuration through which the stabilizing member 12 is receivable. Upon inserting the stabilizing member 12 through the central lumen of the reel 70A, the housing 80A is adapted to be clamped onto the stabilizing member 12 with the reel 70A free to rotate about the stabilizing member 12.

The first connector 22A is attached or secured to the reel 70A and passes out of the housing 80A through an appropriately sized opening in the housing 80A. Actuation of the vertical gear 74A via the actuation head 78A turns the circumferential gear 72A, which turns the reel 70A, thus winding (or unwinding, depending on the direction in which the reel 70A is turned) the first connector 22A about the reel 70A. Rotation of the reel 70A in the appropriate direction draws the first connector 22A in toward the first tensioner 20A, pulling the first correction anchor 18A (FIG. 1) toward the first tensioner 20A according to some methods of correcting a spinal defect. In some embodiments, the actuation head 78A has a receptacle for receiving a hex head driver for rotating the actuation head 78A.

From the foregoing, it should also be understood that the second connector 22B is similarly coupled to the second tensioner 20B, where actuation of the second tensioner 20B modifies the effective length of the second connector 22B, drawing the connector 22B in or letting them out.

The connectors 22A, 22B are optionally substantially similar, and thus various features of the connectors 22 are described in association with the first connector 22A. Features of the first connector 22A are designated with reference numbers followed by an "A" and similar features of the second connector 22B are designated with similar reference numbers followed by a "B."

In some embodiments, the first connector 22A is substantially flexible such that the first connector 22A is able to be pivoted in multiple directions (e.g., to facilitate a polyaxial connection to the correction anchor 18A and/or the tensioner 20A). Such flexibility additionally or alternatively facilitates spooling or winding of the first connector 22A, for example. Suitable flexible materials for forming the first connector 22A include wire and stranded cables, monofilament polymer materials, multifilament polymer materials, multifilament carbon or ceramic fibers, and others. In some embodiments, the first connector 22A is formed of stainless steel or titanium wire or cable, although a variety of materials are contemplated.

As shown in FIG. 1, the first connector 22A, also described as a force directing member or a cable, is adapted to be secured to the first correction anchor 18A and the first tensioner 20A, the first connector 22A defining an effective length between the first tensioner 20A and the first correction anchor 18A, and thus the stabilizing member 12 (although, in some embodiments, the first connector 22A is secured directly to the stabilizing member 12). As described, in some embodiments, the first tensioner 20A is adapted to modify, and provides means for modifying, the effective length of the first connector 22A. As shown, the second connector 22B interacts similarly with the second correction anchors 18B.

In view of the foregoing, assembly and use of the system 10 according to some embodiments generally includes attaching the stabilizing anchors 14 on superior and/or inferior locations of the target region 24A, for example to transitional vertebrae characterizing a scoliotic curvature of the spinal column 24. In some embodiments, the target region 24A includes those of the vertebrae 26 in need, or in greater need, of correction. In operation, the connectors 22 couple the correction anchors 18 to the stabilizing member 12 and, by retracting the connectors 22 toward the stabilizing member 12, the spinal column 24 is brought into more natural alignment.

The system 10 is optionally used for incremental correction, for gross correction, and/or for maintaining a correction as desired. For example, the connectors 22 are optionally retracted incrementally as part of one or more procedures using the tensioners 20. In other embodiments, a single, gross adjustment is made using the tensioners 20 or other device(s) to accomplish a desired correction. In still other embodiments, a correction is made using other hardware, prior to or in conjunction with securing the system 10 to the spinal column 24, where the system 10 is utilized to maintain the desired correction.

Figure 5:
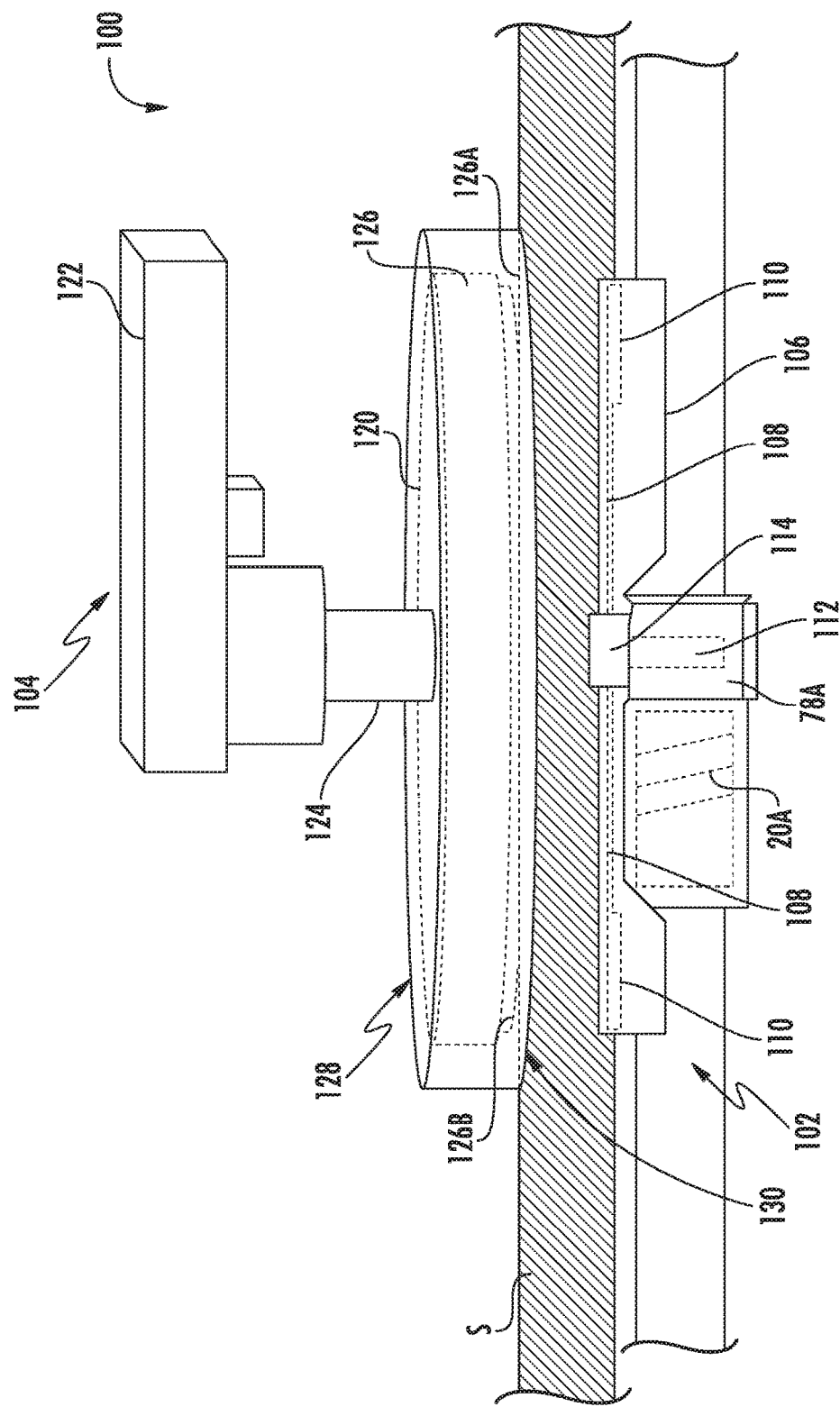
FIGS. 5 and 6 show a tensioning system for externally actuating one or more of the tensioners of the system of FIG. 1, following implantation of the system, according to some embodiments.
Figure 6:
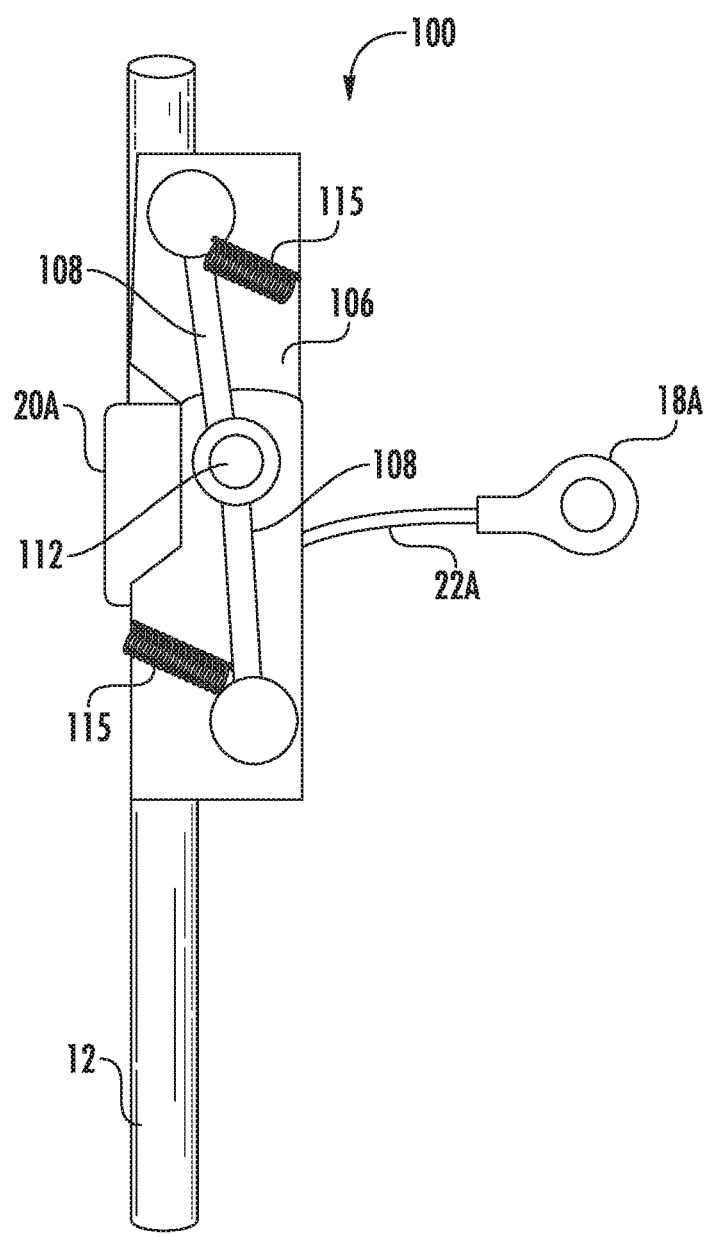

FIGS. 5 and 6 show a tensioning system 100 for externally actuating one or more of the tensioners 20 following implantation of the system 10. As shown, the tensioning system 100 includes an implantable driver 102, also described as a reciprocating adjuster, and an external driver 104.

In some embodiments, the implantable driver 102 includes a housing 106, one or more lever arms 108, also described as piston units, maintaining one or more magnet(s) 110 and defining a center of rotation within the housing 106, a drive shaft 112 coaxial with the center of rotation of the lever arms 108, a one-way roller clutch 114 connected to the drive shaft 112, and reset springs 114 (FIG. 6), also described as a return mechanism. The drive shaft 112 is adapted to couple with the actuation head 78A, for example by including a suitable mating component, such as a hex head driver, or by being integrally formed or otherwise connected to the actuation head 78A such that displacement of the lever arms 108 in a first direction causes the reel 70A to rotate in a second, orthogonal direction such that the tensioner 20A acts as a transfer unit. In some embodiments, the housing 106 of the implantable driver 102 is secured to the housing 80A, for example being integrally formed therewith.

The external driver 104 is configured to activate the implantable driver 102 through the body of a patient (e.g., through skin, muscle, and/or bone as appropriate) and includes a housing 120, a drive assembly 122, a drive shaft 124 connected to the drive assembly 122, and a magnet assembly 126 connected to the drive shaft 124. In use, activation of the drive assembly 122 causes the magnet assembly 126 to rotate.

The drive assembly 122 is optionally an angle driver adapted to rotate the drive shaft 124 at a desired speed and torque. The housing 120 is optionally substantially cylindrical in shape and includes a top 128 and a bottom 130, the housing including a central aperture for receiving the drive shaft 124 and being sized and shaped to receive the magnet assembly 126 such that the magnet assembly 126 is free to rotate within the housing 120.

The magnet assembly 126 includes a plurality of magnets, such as a first magnet 126A of a first polarity and a second magnet 126B of the same, or an opposite polarity. As shown in FIG. 5, the first and second magnets 126A, 126B are connected to one another with a circular attachment 128 that is, in turn, connected to the drive shaft 124, the drive shaft 124 being coaxial with an axis of rotation of the magnet assembly 126. The first and second magnets 126A, 126B are optionally diametrically opposed to one another relative to the axis of rotation of the magnet assembly 126.

In some uses, the implantable driver 102 is operated, or magnetically powered, through the skin S of a patient using the external driver 104. In particular, as the first and second magnets 126A, 126B of the external driver 104 rotate, the magnet(s) 110 of the implantable driver 102 are rotated until the magnet(s) 110 are unable to rotate further (e.g., with the housing 106 acting as a stop). The one-way roller clutch 114 allows rotation in a single direction and, upon reaching the limit of rotation, the magnet(s) 110 reset back to their original position via spring-action before the next one of the first and second magnets 126A, 126B rotates into position with one or more of the magnet(s) 110 to initiate another ratchet sequence. The one-way roller clutch 114 is adapted to ratchet, or hold, after a small amount of rotation. This helps allow a relative compact design, as the lever arms 108 are not required to travel through a large rotational angle. For example, the lever arms 108 optionally each travel through an angle of between 0 and 45 degrees or between 5 and 30 degrees, although a variety of angular limits are contemplated. In some embodiments, a gearing system (not shown) is also employed to help increase torque as desired. The housing 106 of the implantable driver 102 and the housing 120 of the external driver 104 help avoid unwanted contact of moving parts with the skin of the patient.

Figure 8:
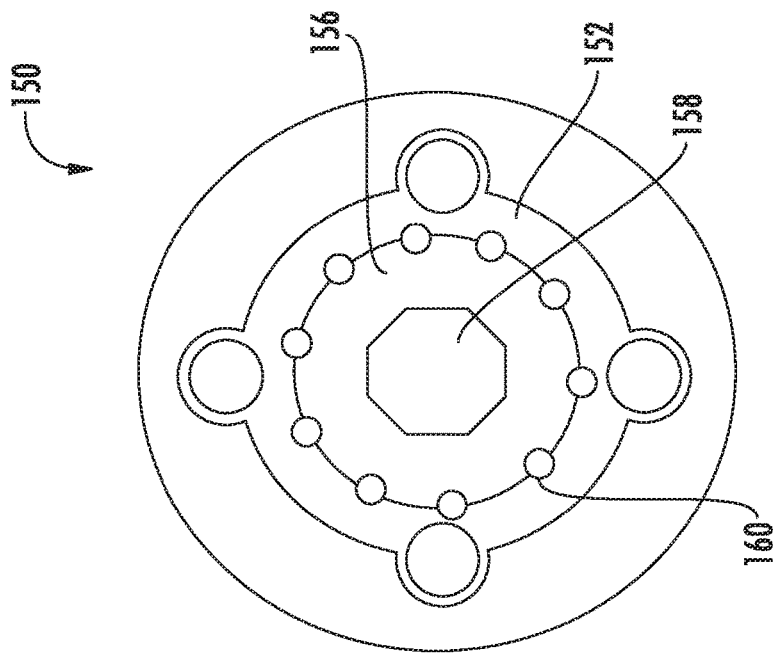
FIGS. 7 and 8 show another tensioning system for externally actuating one or more of the tensioners of the system of FIG. 1, following implantation of the system, according to some embodiments.
Figure 7:
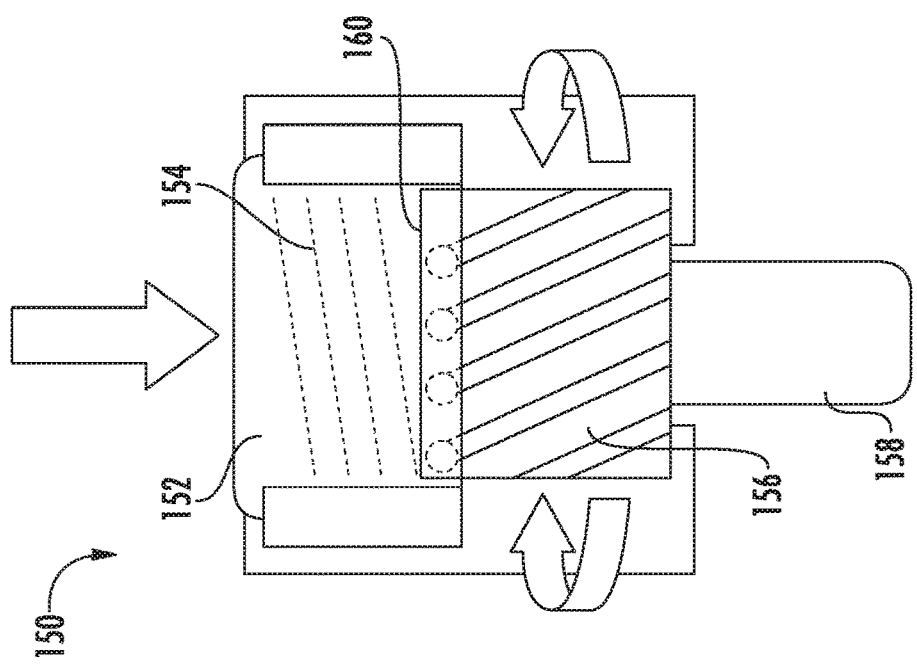

FIGS. 7 and 8 show another tensioning system 150 for externally actuating one or more of the tensioners 20 following implantation of the system 10. As shown, the tensioning system 150 acts as a reciprocating adjuster and includes a cap 152, also described as a piston unit, and a spring 154, also described as a return mechanism, as well as a one-way drive roller clutch 156 and a drive shaft 158, also described as a transfer unit. The tensioning system 150 is adapted to translate a linear downward force to lateral, or transverse, rotation. The cap 152 is engaged with the spring 154 and one-way drive clutch 156 such that when a downward force is applied to the spring-loaded cap 152 the ensuing downward movement of the cap 152 causes lateral rotation of the one-way drive roller clutch 154. In some embodiments, the clutch 156 has grooves or ridges 156A that are cut at an angle so that depression of the cap 152 causes the clutch 156 to rotate, where the steeper the angle the less the force required to depress the cap 152 and the less ensuing rotation of the drive shaft 158. The drive shaft 158 and/or clutch 156 are also optionally coupled to a gearbox (not shown) to enhance mechanical advantage of the system 150. The system 150 also optionally includes a plurality of low-friction ball bearings 160 between the cap 152 and the clutch 156 to reduce the force needed to depress the cap 152 and rotate the drive shaft 158.

The one-way drive roller clutch 156 is coupled to the drive shaft 158 such that rotation of the clutch 156 translates to rotation of the drive shaft 158. In some embodiments, the drive shaft 158 is adapted to be connected to the actuation head 78A. The drive shaft 158 is optionally a 4 mm hex drive adapted, for example, to engage with a female 4 mm hex pocket in the actuation head 78A of the tensioner 20A (FIG. 1).

The system 150 is optionally activated by depressing the button through a patient's skin, where the cap 152 is located by a user via tactile feel and/or external markings (e.g., tattoos), for example. In some embodiments, during use, the cap 152 does not rotate relative to the tensioner 20A. For example, the downward force on the cap 152 rotates the one-way roller clutch 156, which then actuates the tensioner 20A to tighten the connector 22A, for example.

Figure 9:
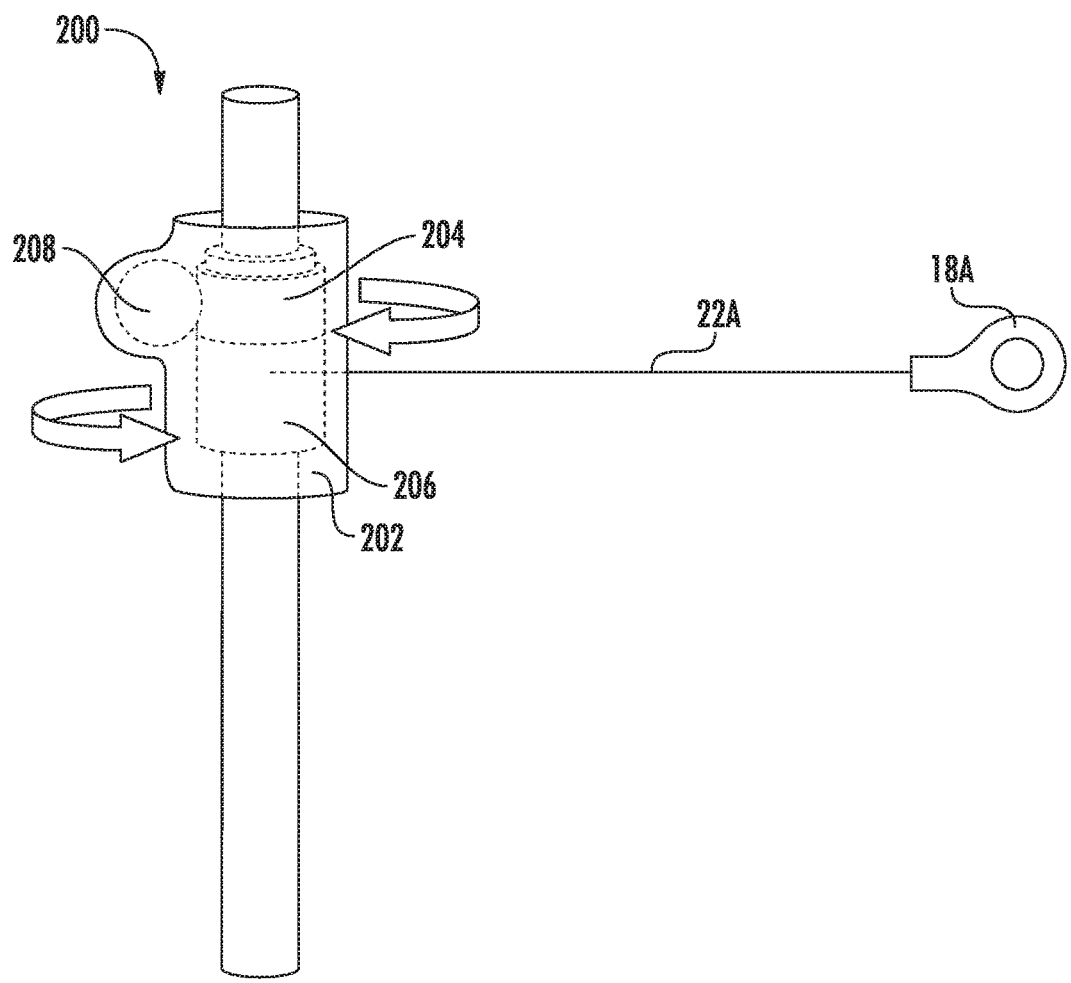
FIGS. 9 and 10 show another tensioning system that is optionally employed in addition to, or as a replacement for, one or more of the tensioners, according to some embodiments.
Figure 10:
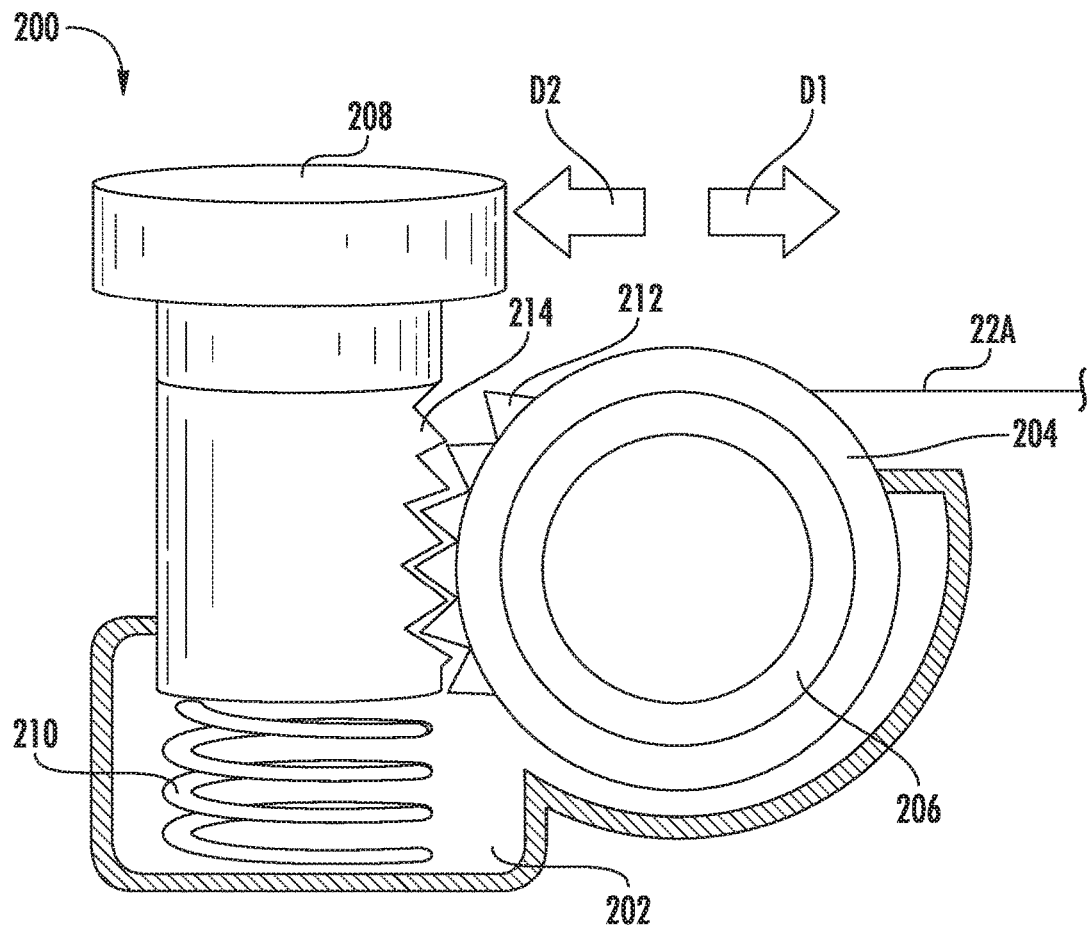

FIGS. 9 and 10 show another tensioning system 200, also described as a reciprocating adjuster, that is optionally employed in addition to, or as a replacement for, one or more of the tensioners 20. The tensioning system 200 includes a housing 202, an outer one-way roller clutch 204, also referred to as an outer clutch, an inner one-way roller clutch 206, also referred to as an inner clutch, a push button 208, also described as a piston unit, and a spring 210, also described as a return mechanism. The housing 202 generally maintains the outer and inner clutches 204, 206, also described as a transfer unit, the push button 208 and the spring 210, and is adapted to be secured (e.g., via a clamshell fit) to the stabilizing member 12. As shown in FIG. 10, the outer clutch 204 includes gearing 212 and the push button 208 includes gearing 214, the gearing 212 and the gearing 214 being adapted to complement one another to rotationally drive the outer clutch 204 upon depressing the push button 208, where linear movement of the push button is translated into transverse movement of the outer clutch 204.

As designated in FIG. 10, the outer clutch 204 is adapted to spin freely in a first direction D1 and to lock to the inner clutch 206 in a second direction D2. In turn, the inner clutch 206 is adapted to spin freely relative to the stabilizing member 12 in the second direction D2 while being locked to the stabilizing member 12 in the first direction D1.

In some embodiments, the outer and inner clutches 204, 206 are one-way drawn-cup roller clutches arranged with the outer clutch 204 around the inner clutch 206 such that when the push button 208 is depressed both the inner roller clutch 206 and the outer clutch 204 forward rotate relative to the stationary member and when the push button is released 208 the spring 210 returns the push button 208 to its original position and the inner clutch 206 remains stationary while the outer clutch 204 back rotates relative to the stabilizing member 12.

One of the connectors 22, for example the connector 22A, is secured to the inner clutch 206 such that a user accessing the push button 208 (e.g., through the skin of a patient as previously described) is able to repeatedly push the push button 208 in order to ratchet the connector 22A toward (or alternatively, away) from the stabilizing rod 12, shortening the effective length of the connector 22A. Gear boxes or other means of enhancing mechanical advantage of the system 200 are employed as desired.

FIGS. 11 and 12 show another tensioning system 250, also described as a reciprocating adjuster, that is optionally employed in addition to, or as a replacement for, one or more of the tensioners 20. As shown, similarly to the system 200, the system 250 also employs a dual roller clutch mechanism, also described as a transfer unit. The system 250 includes a housing 252, an outer one-way roller clutch 254, also referred to as an outer clutch, an inner one-way roller clutch 256, also referred to as an inner clutch, a push button 258, also referred to as a piston unit, a spring 260, also described as a return mechanism, and a drive linkage 262 coupling the push button 258 to the outer clutch 254. In operation, depression of the push button 258 results in rotational force on the outer clutch 254 in a first direction and releasing the push button 258 from the depressed position to an initial position results in a rotational force on the outer clutch 254 in an opposite direction. The housing 252 generally maintains the outer and inner clutches 254, 256, the push button 258, the spring 260, and the drive linkage 262, and is adapted to be secured (e.g., via a clamshell fit) to the stabilizing member 12. As shown, the system 250 also includes a magnetic latch assembly 270 adapted to allow selective activation of the system 250 for adjustment.

In some embodiments, the system 250 generally operates similarly to the system 200, where a user depresses the push button 258 through the skin of the patient to ratchet one of the connectors 22, for example the first connector 22A, around the inner clutch 254. Additionally, the magnetic latch assembly 270 is present as an optional feature to help prevent inadvertent adjustment of the system 250 (e.g., by an unintentional depression of the push button 258). As shown, the magnetic latch assembly 270 includes a housing 271 maintaining a spring 272, a latch magnet 274, and a stop member 276 adapted to engage with stop features 280 associated with the inner clutch 256 (e.g., slots formed into the outer surface of the inner clutch 256).

The magnetic latch assembly 274 is operated by bringing a magnet in close enough proximity to the latch magnet 274 to release the stop member 276 from the stop features 280. Upon doing so, the push button 258 is able to be depressed to ratchet the system 250.

Thus, the system 250 provides a relatively vertical, or in-line arrangement of a dual roller clutch mechanism, where the push button 258 is more in line with the stabilizing member 12 to help minimize the amount of lateral space taken up by the design. In some embodiments, the magnetic latch assembly 274 helps prevent rotation unless a magnet is placed above the latch magnet 274, thereby helping to prevent unintentional activation of the tensioning system 250. In use, a user (not shown) would bring an external magnet into proximity with the latch magnet to put the system 250 into an active state and then operate the system 250 with the system 250 in the active state.

Figure 14:
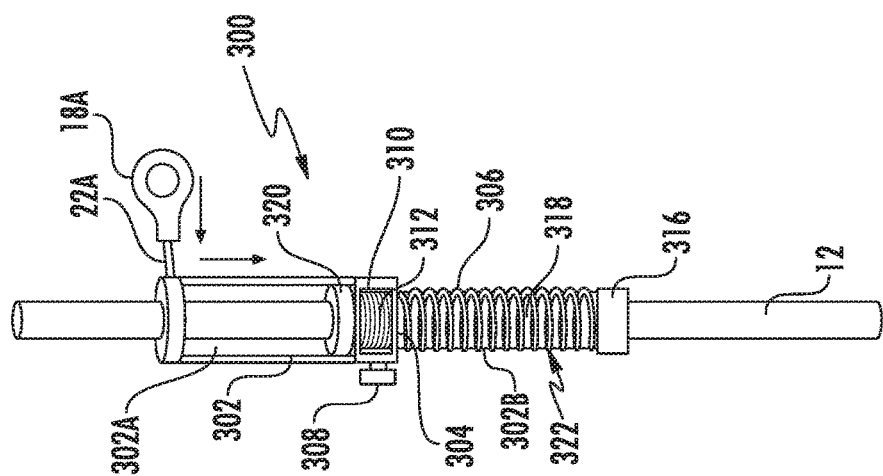
FIGS. 13, 14, and 15 show another tensioning system that is optionally employed in addition to, or as a replacement for, one or more of the tensioners, according to some embodiments.
Figure 13:
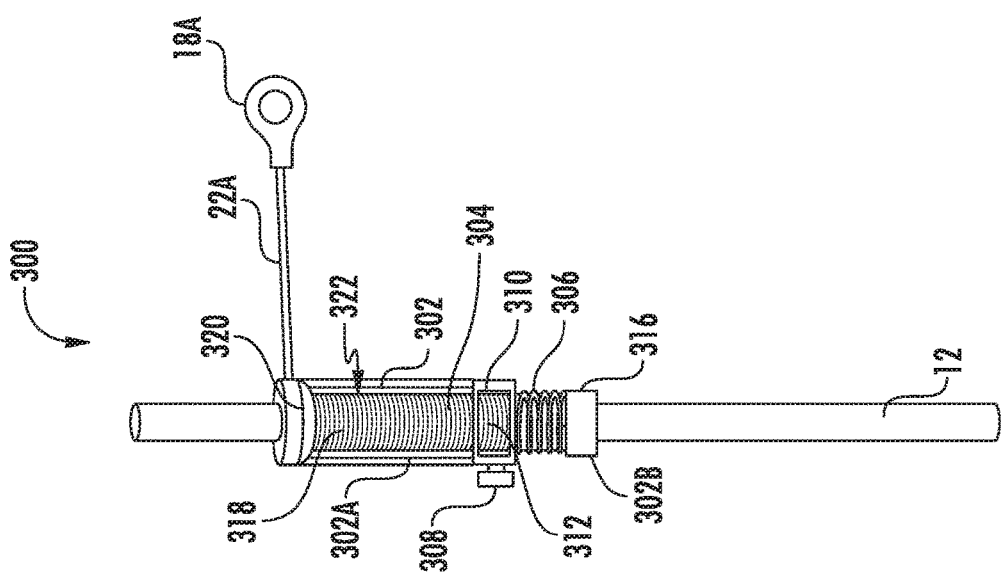
Figure 15:
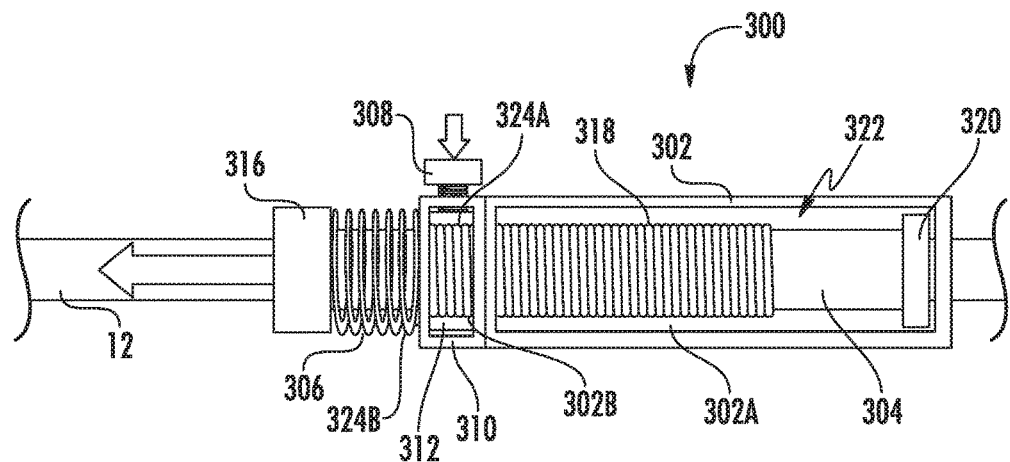

FIGS. 13, 14, and 15 show another tensioning system 300 that is optionally employed in addition to, or as a replacement for, one or more of the tensioners 20. As shown, the system 300, also described as a resistance adjuster and a reciprocating adjuster, includes a housing 302, a drive member 304, also described as a slide unit, a drive spring 306, also described as a potential energy drive, a reset spring 310 (FIG. 15), also described as a return mechanism, and a push button 308 and an engagement member 312, also described as a resistance unit.

The housing 302 is optionally substantially cylindrical and hollow, defining a first compartment 302A and a second compartment 302B. The drive member 304 extends from the first compartment 302A out of the second compartment 302B of the housing 302, where the drive member 304 and the housing 302 are coaxially received over the stabilizing member 12. The drive member 304 is optionally substantially cylindrical and hollow and defines an enlarged base 316, a main body 318, and an enlarged head 320. The main body 318 includes a plurality of teeth 322 (FIG. 15) adapted to selectively engage with the engagement member 312.

As shown in FIGS. 13 and 14, the drive member 304 is adapted to slide over the stabilizing member 12 while the housing 302 is secured relative thereto, the drive member 304 being able to slide out from the housing 302 until the enlarged head limits further travel of the drive member 304. As shown, the drive spring 306 is coaxially received over the drive member 304 between the base 316 and the housing 302. The drive spring 306 is a compression spring for exerting a pushing force on the base 316 of the drive member 304, to move the drive member 304 from a first position (FIG. 13) to a second position (FIG. 14) away from the housing 302, although other types of potential energy drives are contemplated.

As shown in FIG. 15, the push button 308 is slidably received through a sidewall of the second compartment 302B and is connected to the engagement member 312. The engagement member 312 includes complementary sets of teeth 324A, 324B to the teeth 322 on the drive member 304. The sets of teeth 324A, 324B are located on opposite portions of the engagement member 312 and are offset slightly from one another. Upon depressing the push button 308 through the skin, the first set of teeth 324A is released from the complementary teeth 322 on the drive member 304 and, in turn, the second set of teeth 324B engage the complementary teeth 322 of the drive member 304. Upon releasing the push button 308, the reset spring 310 causes the first set of teeth 324A to reengage with the complementary teeth 322 and the second set of teeth 324B to release from the complementary teeth 322. In this manner, the drive member 304 is selectively released (e.g., a relatively small amount) following each cycle of depressing and releasing the push button 308.

One of the connectors 22, such as the first connector 22A is secured to the enlarged head 320. An aperture, roller, or other transition (not shown) is provided on the housing 302 such that the connector 22A is able to extend outwardly, in a transverse direction from the housing 302. As the drive member 304 pistons downwardly out from the housing 302, the enlarged head 320 moves downwardly, pulling the first connector 22A into the housing 302 and reducing the effective length of the first connector 22A between the stabilizing member 12 and the first correction anchor 18A, for example.

Though not shown, a magnetic latch assembly, such as those previously described, is optionally employed with this embodiment, or any other appropriate embodiment, to help prevent inadvertent actuation of the tensioning system 300. Moreover, although the pushing force is supplied by the drive spring 306, in other embodiments the pushing force is supplied by other potential energy drives, including expansion of a hydrogel material, gas (e.g., pre-installed in the first compartment 302A or generated via chemical reaction, for example), or other means for generating a pushing force on the drive member 304.

Figure 16:
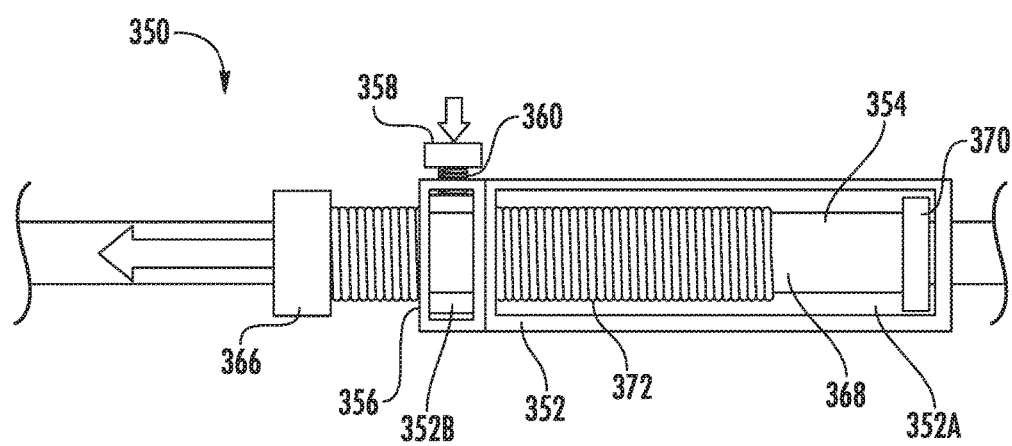
FIGS. 16 and 17 show another tensioning system that is optionally employed in addition to, or as a replacement for, one or more of the tensioners, according to some embodiments.
Figure 17:
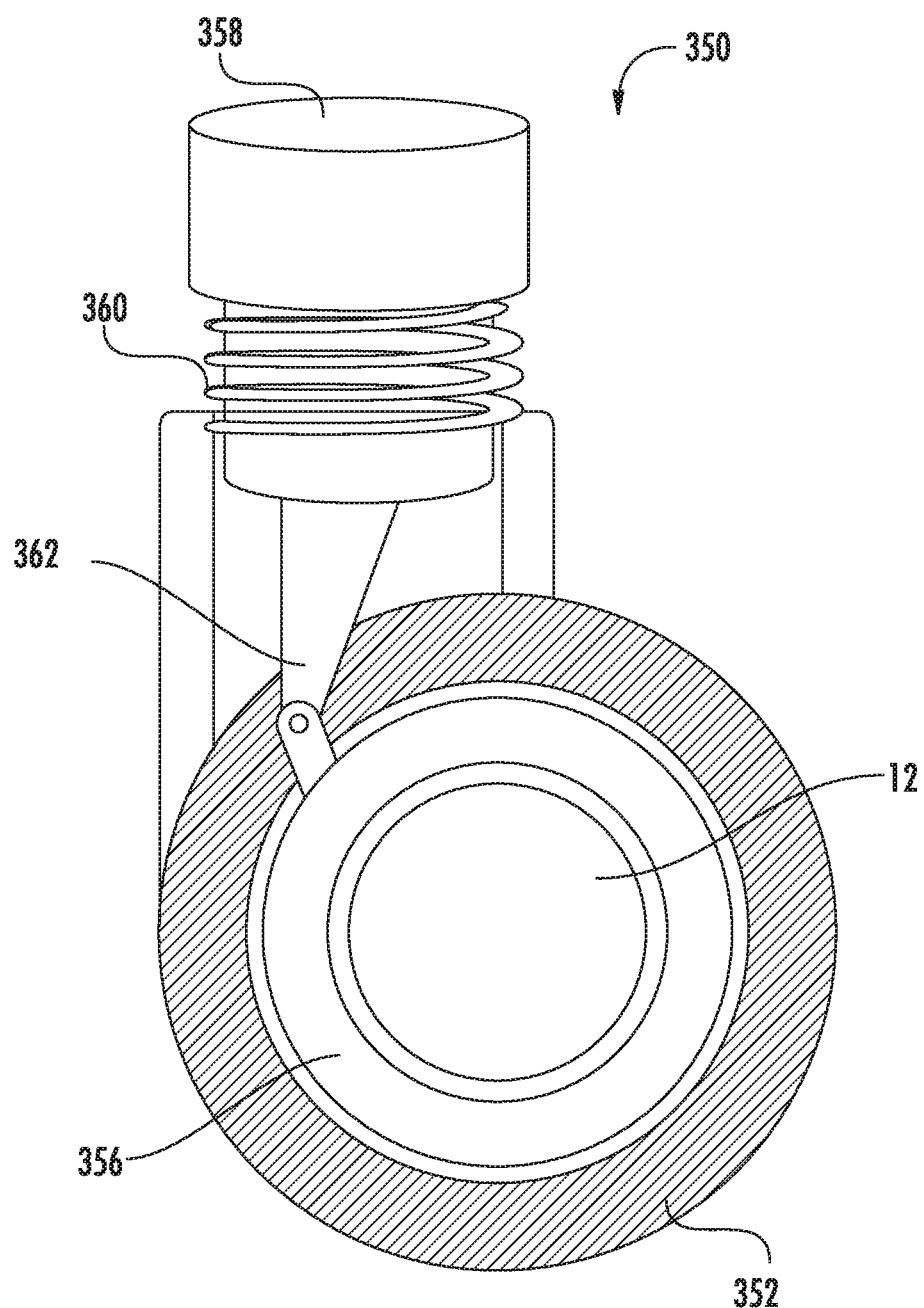

FIGS. 16 and 17 show another tensioning system 350 that is optionally employed in addition to, or as a replacement for, one or more of the tensioners 20. The system 350, also described as a reciprocating adjuster, includes a housing 352, a drive member 354, a one-way roller clutch 356, also referred to as an outer clutch, a push button 358, a reset spring 360, also described as a return mechanism, and a drive linkage 362 coupling the push button 358 to the outer clutch 356 such that depression of the push button 358 (e.g., through the skin of a patient) results in rotational force on the outer clutch 356 in a first direction and releasing the push button 358 from the depressed position to an initial position resulting in a rotational force on the outer clutch 356 in an opposite direction. The housing 352 generally maintains the outer clutch 356, the push button 358, the reset spring 360, and the drive linkage 362, and is adapted to be secured (e.g., via a clamshell fit) to the stabilizing member 12.

The housing 352 is optionally substantially cylindrical and hollow, defining a first compartment 352A and a second compartment 352B. The drive member 354 is also optionally cylindrical and hollow, the drive member 354 extending from the first compartment 352A out of the second compartment 352B of the housing 352, where the drive member 354 and the housing 352 are coaxially received over the stabilizing member 12. The drive member 354 defines an enlarged base 366, a main body 368, and an enlarged head 370. In some embodiments, one or more of the connectors, such as the first connector 22A, is secured to the enlarged head 370. The main body 368 includes a plurality of threads 372 (FIG. 15) adapted to mate with the outer clutch 356.

The drive member 354 is adapted to slide over the stabilizing member 12 while the housing 352 is secured relative thereto, the drive member 354 being able to slide out from the housing 352 until the enlarged head limits further travel of the drive member 354. As shown, the outer clutch 356 is coaxially received over the drive member 354 between the base 366 and the housing 352. The outer clutch 356 has a threaded internal lumen (not shown), where the threads of the outer clutch 356 mate with the threads 372 of the drive member 354 to move the drive member 304 from a first position to a second position away from the housing 352.

As shown in FIG. 17, the push button 358 is slidably received through a sidewall of the second compartment 352B and is connected to the drive linkage 362. Upon depressing the push button 308, the drive linkage 362 causes the outer clutch 356 to rotate, or ratchet, until the push button 308 is fully depressed. As the outer clutch 356 rotates, the drive member 354 is driven out of the housing 352 and the first connector 22A is pulled into the housing 352, thereby shortening its effective length. In at least this manner, the system 350 is optionally used to tension the first connector 22A to help correct a spinal deformity.

Though not shown, a magnetic latch assembly, such as those previously described, is optionally employed with this embodiment, or any other embodiment described herein, to help prevent inadvertent actuation of the tensioning system 350.

Figure 19:
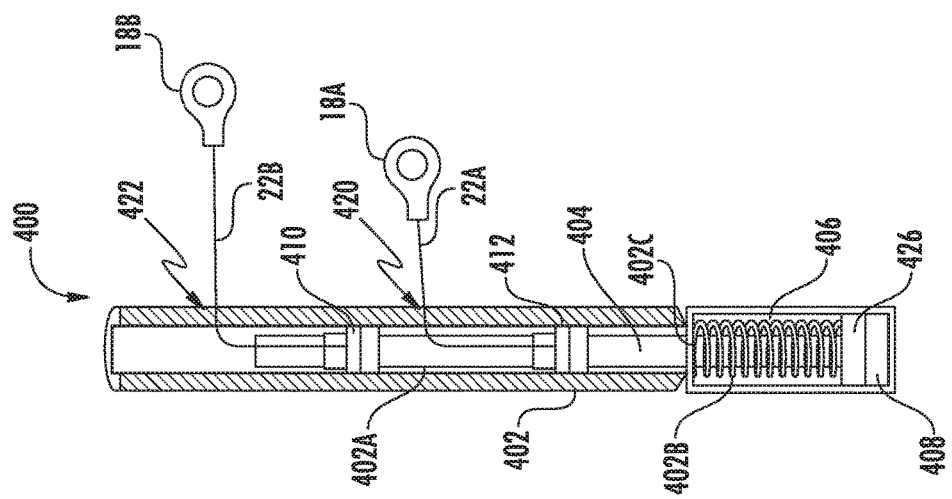
FIGS. 18 and 19 show another tensioning system that is optionally employed in addition to, or as a replacement for, one or more of the tensioners, according to some embodiments.
Figure 18:
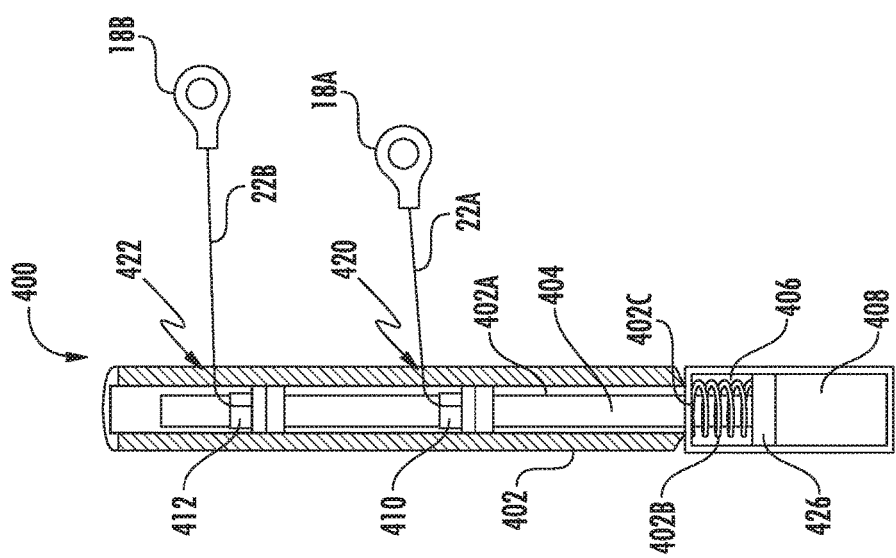

FIGS. 18 and 19 show another tensioning system 400 that is optionally employed in addition to, or as a replacement for, one or more of the tensioners 20. The system 400, also described as a resistance adjuster, includes a hollow portion 402 of the stabilizing member 12, also described as a housing, a drive member 404, also described as a slide unit, a drive spring 406, also described as a potential energy drive, a biodegradable mass 408, also described as a resistance unit, a first collar 410, and a second collar 412.

As shown, the housing 402 defines a first compartment 402A and a second compartment 402B separated by a wall 402C having a lumen (not shown) sized to slidably receive the drive member 404. The housing 402 also includes a first connector aperture 420 and a second connector aperture 422, the first and second connector apertures 420, 422 being adapted to slidably receive one of the connectors 22, such as the first connector 22A and the second connector 22B, for example.

As shown, the drive member 404 extends within the first compartment 402A and the second compartment 402B, where the drive member 404 includes an enlarged base 426 slidably received in the second compartment 402B and abutted against the biodegradable mass 408.

The drive spring 406 is optionally a compression spring received over the drive member 404, the drive spring 406 being positioned between the enlarged base 426 of the drive member 404 and the wall 402C.

In some embodiments, the biodegradable mass 408 is a polymeric material configured to be absorbed into the body over a predetermined time period. For example, in some embodiments, the biodegradable mass 408 is PGA (poly glycolic acid) with a degradation time between about 6 to about 12 months, PLA (poly lactic acid) with a degradation time greater than about 24 months, or a bacterial polyester (e.g., a polyhydroxyalkanoate) with a degradation time greater than about 12 months. The biodegradable mass 408 can be tailored (e.g., with a pre-selected timing by combining different types of materials) to degrade over a predetermined time period. In some embodiments, one or more portion(s) of the housing 402 allows bodily fluids to interact with the biodegradable mass 408. For example, the second compartment 402B optionally a porous wall structure or otherwise allows the body to interact sufficiently with the biodegradable mass 408 to result in absorption of the material.

The first and second collars 410, 412 are positioned along the drive member 404 and, in some embodiments, are secured to the drive member 404 such that the first and second collars 410, 412 move with the drive member 404 as the drive member 404 slides in the housing 402. In turn, the first and second connectors 22A, 22B are secured to the first and second collars 410, 412.

In some implementations, the biodegradable mass 408 begins to be absorbed over time, allowing the drive spring 406 to push the enlarged base 426 downward, in turn causing the drive member 404 to slide downward along with the first and second collars 410, 412. Generally, potential energy is stored in the drive spring 406 or other means for storing energy (e.g., an expandable hydrogel) and is released at the rate of decay of the biodegradable mass 408 (e.g., a substantially continuous and predetermined rate of decay). The rate of decay or degradation can be controlled by the type of biodegradable material used, material geometry, the surface area exposed, the porosity of the material, and the shape of the biodegradable mass 408, for example.

In some embodiments, the axial movement of the drive member 404 draws the connectors 22A, 22B into the housing 202 through the first and second connector apertures 420, 422. As the connectors 22A, 22B are drawn into the housing, the effective length between the connectors 22A, 22B and the first and second correction anchors 18A, 18B is shortened, the correction anchors being drawn toward the housing 402, and consequently, the stabilizing member 12. In at least this manner, the correction anchors 18 are able to be pulled toward the stabilizing member 12, according to some embodiments.

Figure 21:
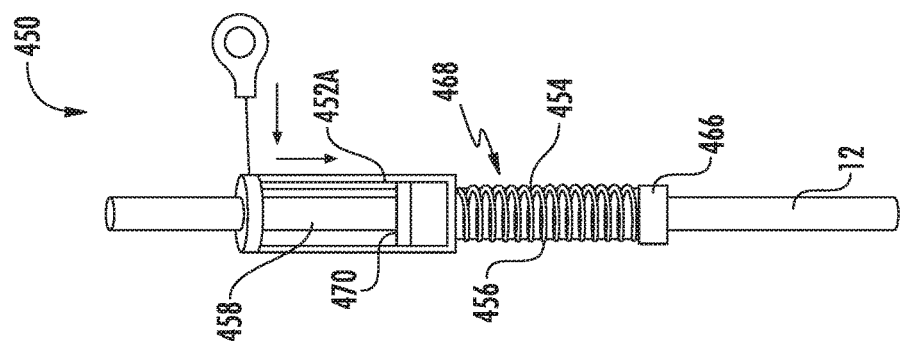
FIGS. 20 and 21 show another tensioning system that is optionally employed in addition to, or as a replacement for, one or more of the tensioners, according to some embodiments.
Figure 20:
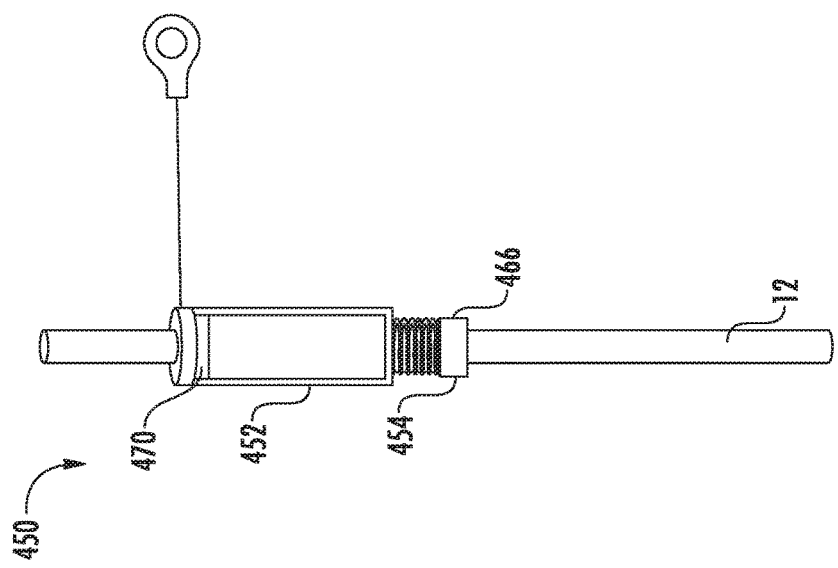

FIGS. 20 and 21 show another tensioning system 450 that is optionally employed in addition to, or as a replacement for, one or more of the tensioners 20. The system 450, also described as a resistance adjuster, includes a housing 452 adapted to be received over the stabilizing member 12, a drive member 454, also described as a slide unit, a drive spring 456, also described as a potential energy drive, and a biodegradable mass 458, also described as a resistance unit. In some embodiments, the system 450 generally operates similarly to the system 400, where the system 450 is adapted to be secured over the stabilizing member 12.

The housing 452 is optionally substantially cylindrical and hollow, defining a first compartment 452A. The drive member 454 extends from the first compartment 452A out of the housing 452, where the drive member 454 and the housing 452 are coaxially received over the stabilizing member 12. The drive member 454 is optionally substantially cylindrical and hollow and defines an enlarged base 466, a main body 468, and an enlarged head 470.

As shown, the drive member 454 is adapted to slide over the stabilizing member 12 while the housing 452 is secured relative thereto, the drive member 454 being able to slide out from the housing 452 until the enlarged head 470 limits further travel of the drive member 454. As shown, the drive spring 456 is coaxially received over the drive member 454 between the base 466 and the housing 452. The drive spring 456 is a compression spring for exerting a pushing force on the base 466 of the drive member 454. The biodegradable mass 458 is located in the first compartment 452A between under the enlarged head 470 to substantially prevent the drive spring 456 from moving the drive member 454. As the biodegradable mass degrades, the resistance to movement is removed and the drive spring 456 is able to move the drive member 454 from a first position (FIG. 20) to a second position (FIG. 21) away from the housing 452, although other types of springs are contemplated.

As the drive member 454 is selectively released (e.g., a predetermined amount over time) following implantation of the system 450, the enlarged head 470 moves within the first compartment 452A. In some embodiments, one or more of the connectors 22, such as the first connector 22A, is secured relative to the enlarged head 470. As the head 470 is actuated within the first compartment 452A, the first connector 22A is drawn into the housing 452, thereby shortening the effective length of the first connector 22A between the stabilizing member 12 and the first correction anchor 18A. Thus, in some embodiments, the system 450 is optionally employed to draw one or more of the correction anchors 18 toward the stabilizing member 12.

FIGS. 22, 23, and 24 show another tensioning system 500 that is optionally employed in addition to, or as a replacement for, one or more of the tensioners 20. The system 500, also described as a resistance adjuster, includes a housing 502 adapted to be received over the stabilizing member 12, a drive member 504, also described as a slide unit, a drive spring 506, also described as a potential energy drive, a biodegradable mass 508, also described as a resistance unit, a drive unit 510 connected to the drive member 504, and a guide piece 512. In some embodiments, the system 500 generally operates similarly to the system 450, the system 500 being adapted to be secured over the stabilizing member 12.

The housing 502 is optionally substantially cylindrical and hollow, defining a first compartment 502A. The drive member 504 extends from the first compartment 502A out of the housing 502, where the drive member 504 and the housing 502 are coaxially received over the stabilizing member 12. The drive member 504 is optionally substantially cylindrical and hollow and defines an enlarged base 516, a main body 518, and an enlarged head 520.

As shown, the drive member 504 is adapted to slide over the stabilizing member 12 while the housing 502 is secured relative thereto, the drive member 504 being able to slide out from the housing 502 until the enlarged head 520 limits further travel of the drive member 504. As shown, the drive spring 506 is coaxially received over the drive member 504 between the base 516 and the housing 502. The drive spring 506 is a compression spring for exerting a pushing force on the base 516 of the drive member 504. The biodegradable mass 508 is located in the first compartment 502A under the enlarged base 516 to substantially prevent the drive spring 456 from moving the drive member 504. As the biodegradable mass 508 degrades, the drive spring 506 is able to move the drive member 504 from a first position to a second position into the housing 502, although other types of springs are contemplated.

As indicated in FIGS. 22 and 23, the drive unit 510 is connected to the drive member 504, the drive unit being slidably received over the stabilizing member 12. The drive unit 510 includes an inner cylinder 530 and with male threading and an outer cylinder 532 with female threading complementary to the male threading on the inner cylinder 530. As shown in FIG. 24, the outer cylinder 532 includes an internal magnet 534 adapted to interact with one or more external magnets 536 adapted to be activated outside the patient, which, when rotated, rotationally drive the internal magnet 534 through the skin of the patient, causing the outer cylinder 532 to be driven up or down the inner cylinder 530.

In some embodiments, the internal magnet 534 has a first portion of a first polarity and a second portion of a second, opposite polarity. The external magnets 536 similarly have two portions with opposite polarities. As the external magnets 536 rotate, the polarities of the external magnets push and pull, respectively, on the polarities of the internal magnet 534 as the external magnets are rotated. One example of a suitable magnetic drive system is described in U.S. Patent Application Publication 2009/0112207, filed May 15, 2008 and published Apr. 30, 2009, the entire contents of which are incorporated herein by reference.

The guide piece 512 is adapted to be a low friction interface for one or more of the connectors 22 adapted to direct the connectors 22 from an axial direction along the stabilizing member 12 to a more transverse direction. One of the connectors 22, such as the first connector 22A, is secured to the outer cylinder 532 and up through the guide piece 512 to one of the correction anchors 18, such as the first correction anchor 18A.

In some embodiments, the drive member 504 is selectively released (e.g., a predetermined amount over time) following implantation of the system 500 such that the enlarged head 520 moves further into the first compartment 502A. As the drive member 504 moves axially, so does the drive unit 510, in turn pulling the connector 22A and shortening the effective length of the connector 22A between the stabilizing member 12 and the correction anchor 18A. As desired, the connector 22A is loosened or tightened (e.g., for fine adjustment purposes), by using the external magnets 536 to rotate the internal magnet 534.

Figure 25:
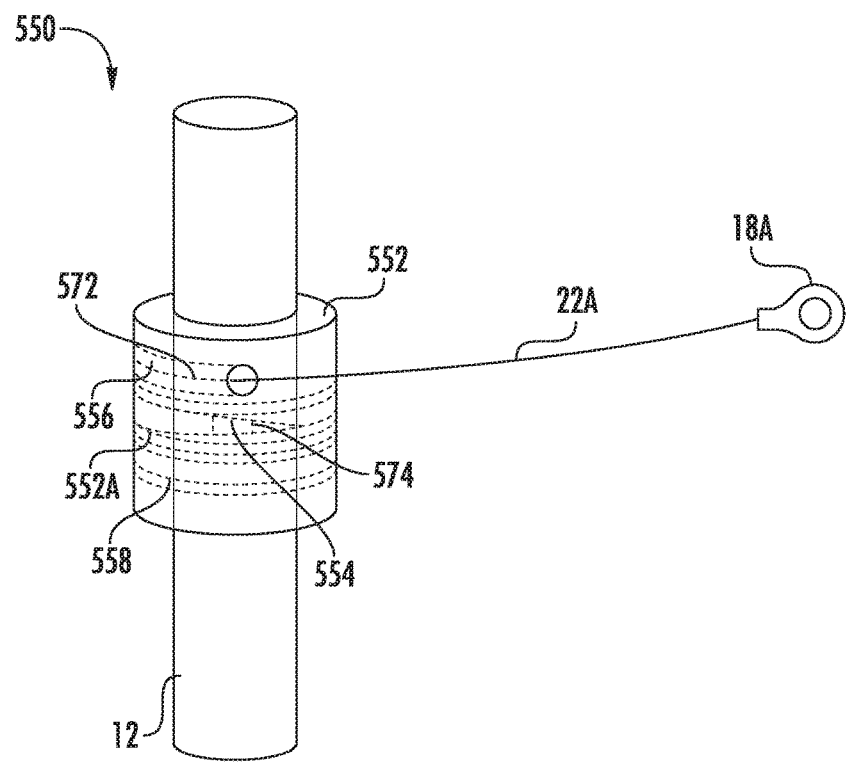
FIGS. 25 and 26 show another tensioning system that is optionally employed in addition to, or as a replacement for, one or more of the tensioners, according to some embodiments.
Figure 26:
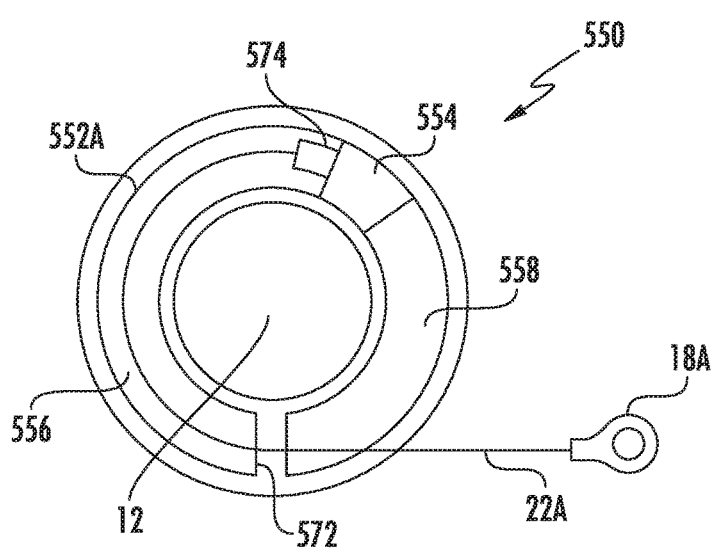

FIGS. 25 and 26 show another tensioning system 550 that is optionally employed in addition to, or as a replacement for, one or more of the tensioners 20. In some embodiments, the system 550, also described as a resistance adjuster, includes a housing 552 adapted to be received over the stabilizing member 12, a coupler 554, also described as a slide unit, a drive spring 556, also described as a potential energy drive, and a biodegradable mass 558, also described as a resistance unit.

In some embodiments, the housing 552 is adapted to be secured to the stabilizing member 12 (e.g., via a clamshell fit) and includes a substantially helical internal compartment 552A with a connector aperture 570 opening into the internal compartment 552A. As shown, the drive spring 556 is helically wound in the internal compartment 552A and is adapted to act as a torsion spring, the drive spring 556 being in a compressed state with a first end 572 of the spring 556 secured to the housing 552 and a second end 574 of the spring 556 connected to the coupler 554. In some embodiments, the biodegradable mass 558 is disposed at the second end 574 of the spring 556 and/or the coupler 554, maintaining the spring 556 in a compressed state. One of the connectors 22, such as the first connector 22A, is secured to the coupler 554, the first connector 22A winding back out of the internal compartment 552A through the connector aperture 570.

In some embodiments, as the biodegradable mass 558 degrades, the second end 570 of the spring 556 travels further into the internal compartment 552A, drawing the coupler 554 and the first connector 22A further into the internal compartment 552A. In some embodiments, as the first connector 22A is drawn into the internal compartment 552A, the effective length between the stabilizer 12 and the correction anchor 18A is reduced.

FIGS. 27 and 28 show an expanding stabilizing member system 600 that is optionally employed in addition to, or as a replacement for, the stabilizing member 12. For example, the system 600, also described as a resistance adjuster, is optionally employed by attaching the system 600 to the spinal column 24 using the stabilizing anchors 18, such that the spinal column 24 is able to be expanded longitudinally to help reduce the defective curvature of the spinal column 24.

In some embodiments, the system 600 includes a housing 602, a drive member 604, also described as a slide unit, a drive spring 606, also described as a potential energy drive, a biodegradable mass 608, also described as a resistance unit, and an adjustable collar 610. The housing 602 is optionally substantially cylindrical and hollow, defining a first compartment 602A. The drive member 604 extends from the first compartment 602A out of the housing 602. The drive member 604 is optionally substantially cylindrical and defines a main body 612 having a plurality of male threads along the length thereof (not shown) and an enlarged head 614.

In some embodiments, the adjustable collar 610 has female threading and is coaxially received over the male threading of the main body 612. The adjustable collar 610 includes a magnetic element and/or is otherwise adapted to respond to magnetic force, the adjustable collar 610 having a first polarity portion 610A and a second polarity portion 610B.

As shown, the drive member 604 is adapted to slide within the housing 602. In some embodiments, the drive member 604 is restricted from rotating relative to the drive housing, for example, being keyed or otherwise having complementary features to the portion of the housing 602 from which the drive member 604 extends that substantially prevent relative rotation between the housing and drive member 604. The drive member 604 is adapted to slide out from the housing 602 until the adjustable collar 610 limits further travel of the drive member 604 and into the housing 602 until the enlarged head 614 abuts the housing 602.

As shown, the drive spring 606 is coaxially received over the drive member 604 between the adjustable collar 610 and the housing 602. The drive spring 606 is a compression spring for exerting a pushing force on the adjustable collar 610 of the drive member 604. The biodegradable mass 608 is located in the first compartment 602A ahead of the adjustable collar 610 to substantially prevent the drive spring 606 from moving the drive member 604. As the biodegradable mass 608 degrades, the drive spring 606 is able to move the drive member 604 from a first position to a second position outwardly from the housing 602, to extend the overall length of the system 600.

In some embodiments, the effective length of the system 600 is adjusted (e.g., for fine adjustments or if the length of the system begins to grow too quickly), by rotating the adjustable collar 610. In some embodiments, an external magnetic drive 640, such as those previously described, is utilized through the skin to rotate the adjustable collar 610 and adjust the overall length of the system 600.

Although potential energy is stored in the system 600 using the spring 606, in other embodiments an expanding material, is utilized to exert a pushing force on the drive member 604. For example a hydrogel material (e.g., material having the tradename "HYPAN" available from Hymedix), NDGA (nordihydroguaiaretic acid), and/or other expandable materials are optionally utilized. In still other embodiments, the spring 606 is replaced and/or augmented by using a compressed gas cylinder or other means for storing potential energy for use in the system 600 to drive the drive member 604.

Figure 29:
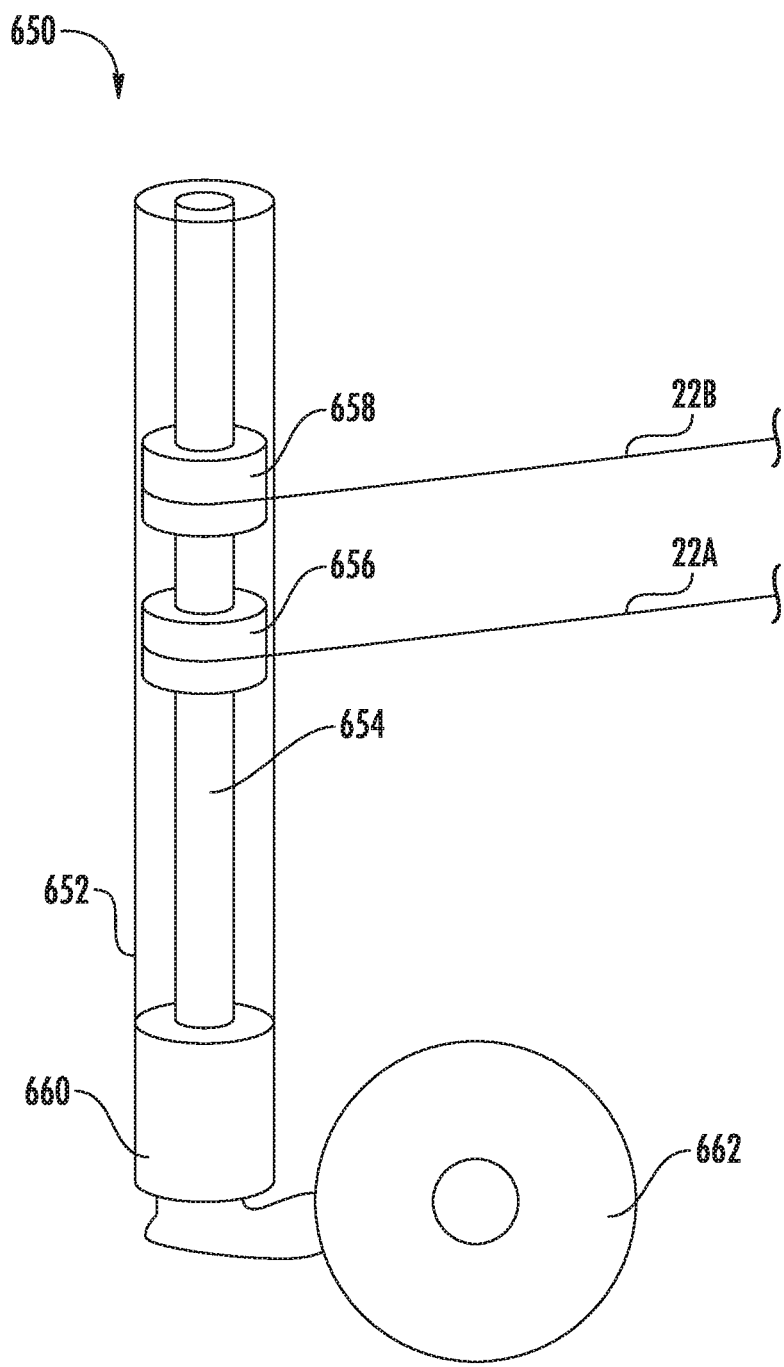
FIG. 29 shows another tensioning system that is optionally employed in addition to, or as a replacement for, one or more of the tensioners, according to some embodiments.

FIG. 29 shows another tensioning system 650 that is optionally employed in addition to, or as a replacement for, one or more of the tensioners 20. For example, the tensioning system 650 optionally replaces the stabilizing member 12 or portions thereof, or is mounted to the stabilizing member 12 as desired. The system 650 includes a housing 652, a drive member 654, a first actuator collar 656, a second actuator collar 658, a motor unit 660 connected to the drive member 654, and a power coupler 662.

In some embodiments, the housing 652 includes a substantially hollow vertical rod (e.g., about 10-15 mm in diameter), the housing 652 being adapted to maintain the drive member 654, the first and second actuator collars 656, 658, and the motor unit 660. The housing 652 optionally acts as the stabilizing member 12 in the system 10, in some embodiments, the housing being secured to the spinal column 24 with the stabilizing anchors 18, for example.

The drive member 654 is optionally adapted to act as a substantially flexible axle, for example being about 3 mm in diameter and formed of steel or other appropriate material (e.g., metallic and/or polymeric materials). The actuator collars 656, 658 are secured to the drive member 654 at longitudinal positions thereon and one or more of the connectors 22, such as the first and second connectors 22A, 22B, respectively, are secured to the actuator collars 656, 658.

The first and second actuator collars 656, 658 are optionally substantially similar, the first and second actuator collars 656, 658 being described cumulatively with respect to the first actuator collar 656. In some embodiments, the first actuator collar 656 is a magnetically activated tensioner means secured to one of the connectors 22, such as the first connector 22A.

Figure 31:
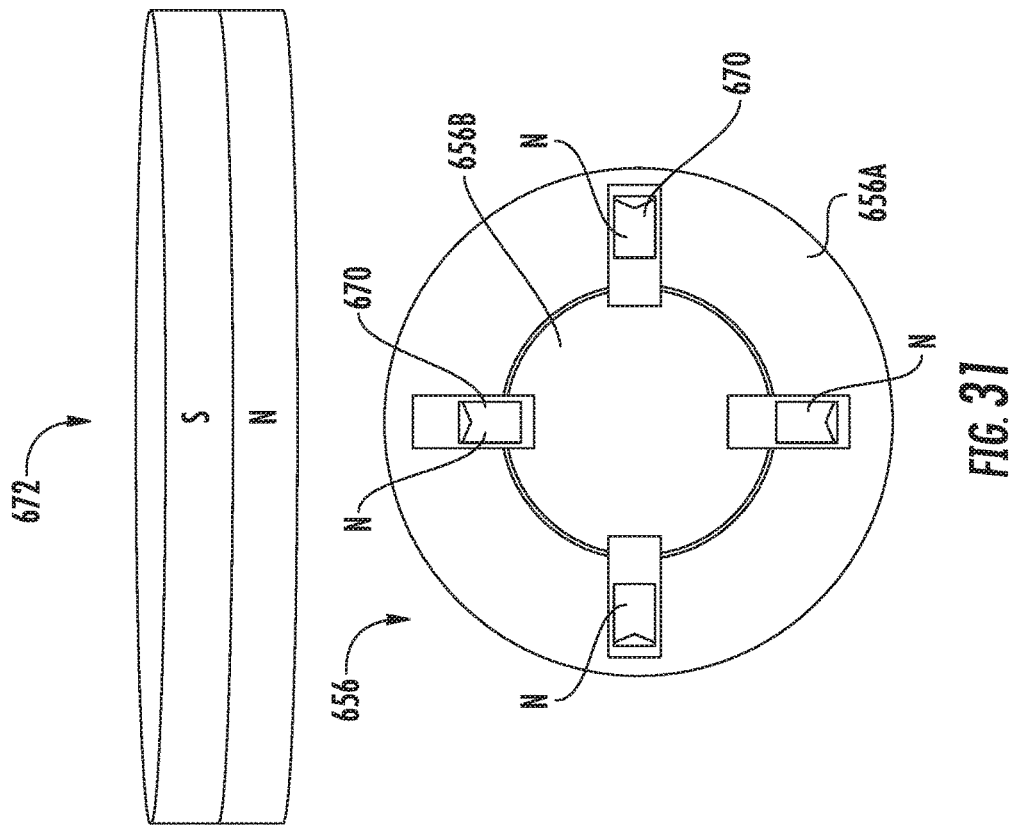
FIGS. 30 and 31 show a first actuator collar of the system of FIG. 29, where
Figure 30:
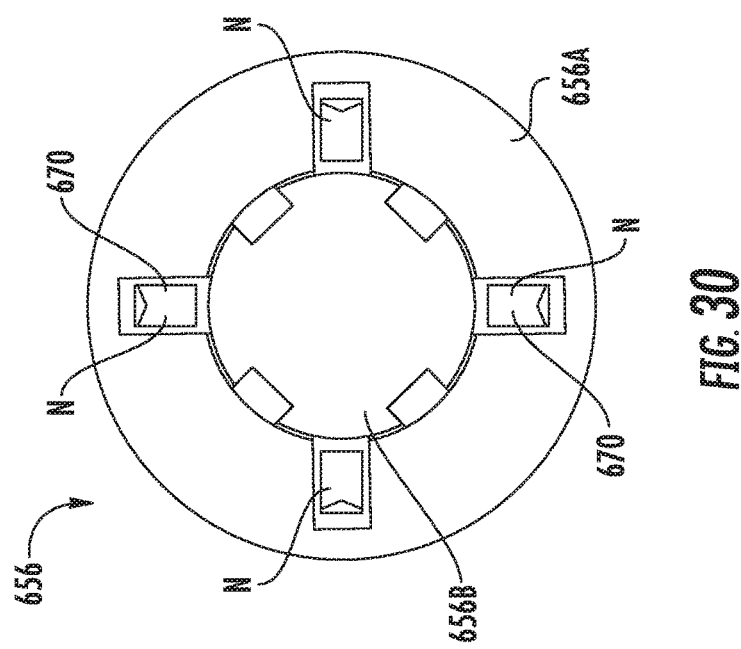

The first actuator collar 656 is shown in FIGS. 30 and 31, where FIG. 30 shows the first actuator collar 656 in a free spinning, or unlocked state, and FIG. 31 shows the first actuator collar 656 in a locked, or engaged state. As shown, the first actuator collar 656 includes an outer portion 656A and an inner portion 656B having a plurality of pockets slidably receiving a plurality of magnetic engagement members 670. As shown in FIG. 31, an external magnet 672 is brought into proximity of a patient (not shown) to cause the magnetic engagement members 670 to push inwardly to lock the inner and outer portions 656A, 656B.

In some embodiments, the magnetic polarity on the external magnet 672 is switched (by physically flipping a magnet or switching the current to an electric magnet) in order to cause the magnetic engagement members 670 to slide outwardly into the pockets in the outer portion 656A to release the first actuator collar 656. As described further below, magnetic activation of the actuator collars 656, 658 helps facilitate individual adjustment, allowing more torque from a single source to be available to draw the connectors 22 to the housing 652.

In some embodiments, the motor unit 660 is a Maxon Motor, 13 mm OD, with a 3371:1 gear ratio, although a variety of motors are optionally employed. The power coupler 662 is optionally an inductive power coupler, also described as a receiver, a secondary coil, or an internal antenna, for receiving inductive power from an external inductive power source (not shown). In some embodiments, the power coupler 662 has about a 50 mm diameter body and includes a physical magnet such that the external inductive power source, or external primary coil, is better able to center on the power coupler 662 to increase the coupling efficiency.

In some embodiments, when the external, primary coil (not shown) is centered above the power coupler 662, electrical energy on the order of 2-3 watts (up to 20 watts if needed) is delivered to the motor unit 660 causing rotation of the drive member 654. The connectors 22 are selectively tensioned by engaging a selected one of the actuator collars 656, 658 magnetically. In at least this manner, power is selectively applied for tensioning so that the maximum amount of tension is directed to the desired connector 22. If desired, the motor unit 660 is reversible and/or gearing (not shown) is employed to pay out, or loosen the connectors 22 as desired. In some embodiments, feedback and position information is transmitted back from the system 650 to an external receiver via IR (infrared) or RF (radio frequency), for example.

Figure 32:
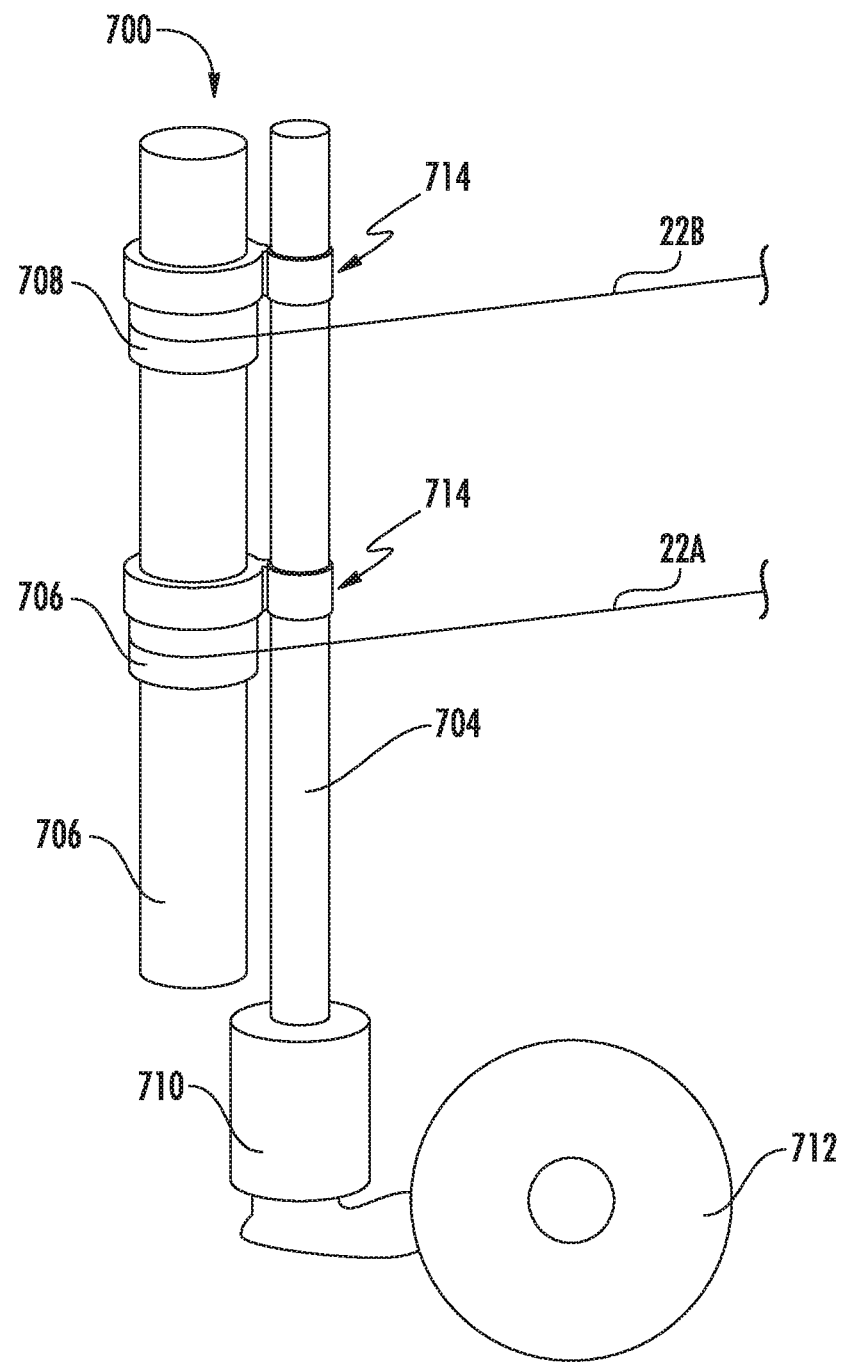
FIG. 32 shows another tensioning system that is optionally employed in addition to, or as a replacement for, one or more of the tensioners, according to some embodiments.

FIG. 32 shows another tensioning system 700 that is optionally employed in addition to, or as a replacement for, one or more of the tensioners 20. For example, the tensioning system 700 optionally replaces the stabilizing member 12 or portions thereof, or is mounted to the stabilizing member 12 as desired. The system 700 includes a secondary spool 702, a drive member 704, a first actuator collar 706, a second actuator collar 708, a motor unit 710 connected to the drive member 704, a power coupler 712, and a gear system 714. Although the power coupler 712 is optionally an inductive power source, in other embodiments the power coupler is an implantable battery or other power source.

As shown, the system 700 operates generally similarly to the system 650. In some embodiments, the drive member 704 and the secondary spool 702 are interconnected by the gear system 714. The motor unit 710 turns the drive member 704, which, through the gear system 714, turns the secondary spool 702. The first and second actuator collars 706, 708 are secured to the secondary spool 702 and are thereby turned to draw one or more of the connectors 22 toward the secondary spool 702. Additionally, the secondary spool 702 is optionally turned in an opposite direction to pay out the connectors 22 from the actuator collars 706, 708 as desired. Magnetic means (not shown) are optionally employed to engage or disengage the actuator collars 706, 708 as desired.

Figure 34:
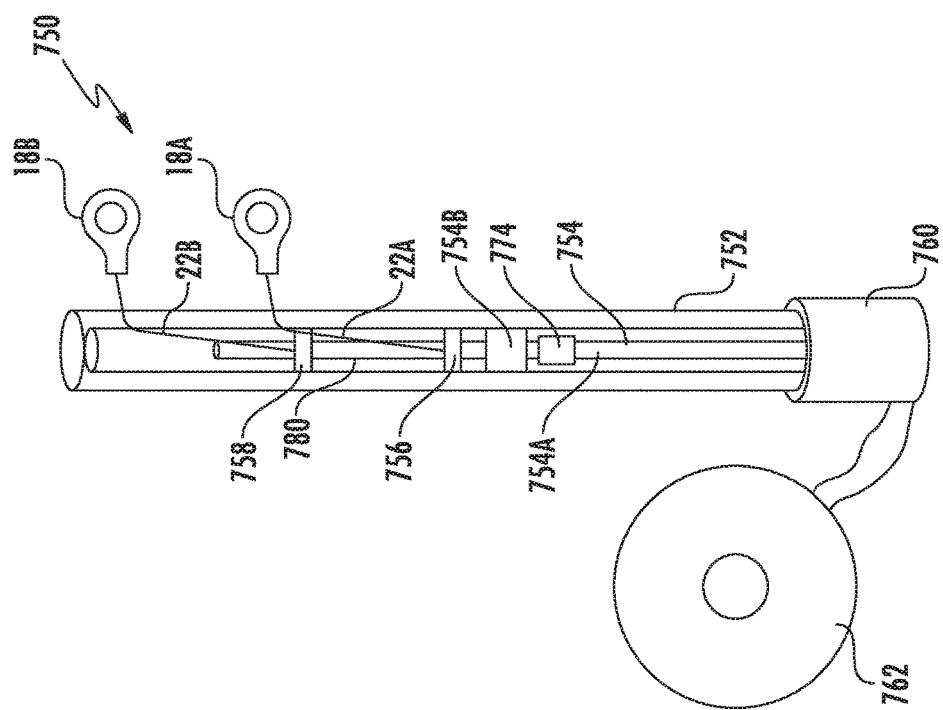
FIGS. 33 and 34 show another tensioning system that is optionally employed in addition to, or as a replacement for, one or more of the tensioners, according to some embodiments.
Figure 33:
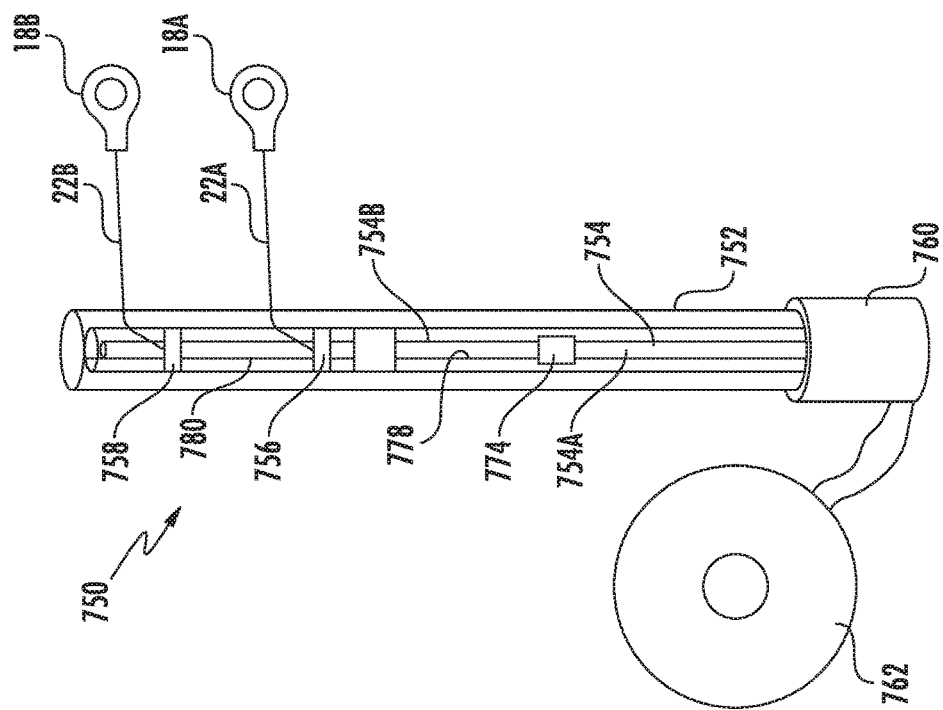

FIGS. 33 and 34 show another tensioning system 750 that is optionally employed in addition to, or as a replacement for, one or more of the tensioners 20. For example, the tensioning system 750 optionally replaces the stabilizing member 12 or portions thereof, or is mounted to the stabilizing member 12 as desired. The system 750 includes a housing 752, a drive member 754, a first actuator collar 756, a second actuator collar 758, a motor unit 760 connected to the drive member 754, and a power coupler 762.

In some embodiments, the housing 752 includes a substantially hollow vertical cylindrical body (e.g., about 10-15 mm in diameter), the housing 752 being adapted to house the drive member 754, the first and second adjustment collars 756, 758, and the motor unit 760. The housing 752 optionally acts as the stabilizing member 12 in the system 10, in some embodiments, the housing being secured to the spinal column 24 with the stabilizing anchors 18, for example.

As shown, the drive member 754 includes two portions, a base portion 754A and a traveler portion 754B. The base portion 754A is elongate and extends from a first end 770 connected to the motor unit 760 and a second end 772 bearing a male threaded head 774. The traveler portion 754A is substantially elongate and includes a female threaded section 778 and a carrier section 780. The traveler portion 754B is non-rotatable and axially slidable in the housing 752. The female threaded section 778 of the traveler portion 754B is mated with the male threaded head 774 of the base portion 754A such that rotation of the base portion 754A by the motor unit 760 causes the traveler portion 754B to move axially within the housing 752. For example, FIG. 33 shows the traveler portion 754B at a first position in the housing 752 and FIG. 34 shows the traveler portion 756B in a second, more retracted position in the housing 752.

The adjustment collars 756, 758 are secured at longitudinal positions along the carrier section 780. One or more of the connectors 22 are secured to each of the adjustment collars, such as the first and second connectors 22A, 22B, respectively, such that axial movement of the carrier section 780 draws in or lets out the connectors 22 from the housing 752, thereby shortening or lengthening the effective length of the connectors 22 between the correction anchors 18 and the housing 752 as desired. In some embodiments, the adjustment collars 756, 758 are also threaded onto the carrier section 780, where rotation of the adjustment collars 756, 758 using external magnets such as those previously referenced, allows additional tensioning and/or loosening of the connectors 22.

FIGS. 35 and 36 show another tensioning system 800 that is optionally employed in addition to, or as a replacement for, one or more of the tensioners 20. For example, the tensioning system 800 optionally replaces the stabilizing member 12 or portions thereof, or is mounted to the stabilizing member 12 as desired. The system 800 includes a housing 802, a drive member 804, a first actuator anchor 806, a second actuator anchor 808, a motor unit 810 connected to the drive member 804, and a power coupler 812.

In some embodiments, the housing 802 includes a substantially hollow vertical cylindrical body (e.g., about 10-15 mm in diameter) having a plurality of connector apertures 816, the housing 802 being adapted to house the drive member 804, the first and second adjustment anchors 806, 808, and the motor unit 810. The housing 802 optionally acts as the stabilizing member 12 in the system 10. In some embodiments, the housing 802 is secured to the spinal column 24 with the stabilizing anchors 18, for example.

As shown, the drive member 804 includes two portions, a base portion 804A and a traveler portion 804B. The base portion 804A is elongate and extends from a first end 820 connected to the motor unit 810 and a second end 822 bearing a male threaded head 824. The traveler portion 804A is substantially elongate and includes a female threaded section 828 and a carrier section 830. The traveler portion 804B is non-rotatable and axially slidable in the housing 802. The female threaded section 828 of the traveler portion 804B is mated with the male threaded head 824 of the base portion 804A such that rotation of the base portion 804A by the motor unit 810 causes the traveler portion 804B to move axially within the housing 802. For example, FIG. 35 shows the traveler portion 804B at a first position in the housing 802 and FIG. 36 shows the traveler portion 806B in a second, more retracted position in the housing 802.

As shown, the first and second adjustment anchors 806, 808 are substantially similar to one another. As such, the second adjustment anchor 808 is described cumulative with respect to the first adjustment anchor 806. The first and/or second adjustment anchors 806, 808 are optionally adapted to be substituted for one or more of the correction anchors 18, according to some embodiments. As shown, the first adjustment anchor 806 is generally L-shaped when viewed from the side, where the first adjustment anchor 806 includes an extension arm 806A with male threading (not shown), a collar 806B with female threading (not shown), a base arm 806C, and a head 806D all assembled together.

The collar 806B is rotatably coupled to the base arm 806C and the extension arm 806A is non-rotatably and slidably coupled to the base arm 806C. The extension arm 806A is received within the collar 806B and the base arm 806C. The threads of the extension arm 806A and the collar 806B are mated such that the extension arm 806A is able to be telescoped inward and outward from the collar 806B and the base arm 806C by rotating the collar 806B in a first direction and a second direction, respectively. The collar 806B is optionally formed of a magnetic material and has a portion with a first polarity and another portion with a second polarity. External magnets (not shown), such as those previously described, are optionally used to rotate the collar 806B to adjust the overall length of the adjustment anchor 806.

The head 806D of the adjustment anchor 806 optionally includes a pedicle screw that is adapted to be driven into a vertebra of the spinal column 24 such that the adjustment anchor 806 is able to be pulled upon similarly to one of the correction anchors 18.

One or more of the connectors 22 are secured to the carrier section 830, respectively, such that axial movement of the carrier section 830 draws in or lets out the connectors 22 from the connector apertures 816 of the housing 802, thereby shortening or lengthening the effective length of the connectors 22 between the adjustment anchors 806A, 806B and the housing 802, and thus the spinal column 24, as desired. Each of the adjustment anchors 806A, 806B are also optionally adjusted in length to modify the tension being exerted by the system 800 on the spinal column 24 as desired.

Figure 37:
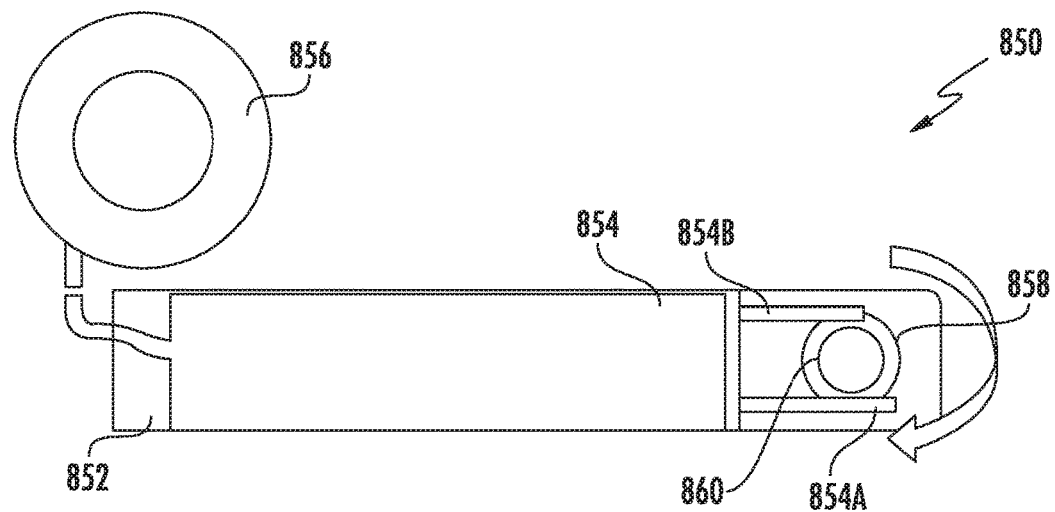
FIGS. 37 and 38 show another tensioning system that is optionally employed in addition to, or as a replacement for, one or more of the tensioners, according to some embodiments.
Figure 38:
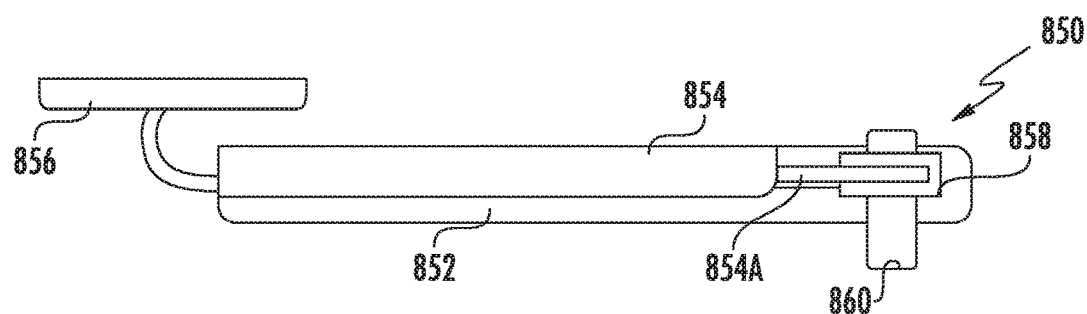

FIGS. 37 and 38 show another tensioning system 850 that is optionally employed as a means for externally operating the tensioners 20. As shown, the system 850, also described as a reciprocating adjuster, includes a housing 852, a motor drive 854, a power coupler 856, a roller clutch 858, and a drive shaft 860.

The housing 852 is adapted to maintain the motor drive 854, the roller clutch 858, and the drive shaft 860. The motor drive 854 is optionally a nitinol drive, such as that sold under the trade name "DM01 nitinol actuator" from "MIGA MOTORS." The motor drive 854 includes an actuation arm 854A and a return spring 854B, also described as a return mechanism, connected on opposite sides of the roller clutch 858.

The power coupler 856 is optionally similar to those previously described (e.g., an induction coil) and, when electrical energy is applied, the nitinol of the motor drive 854 is heated, causing contraction of the actuation arm 854A which pulls the actuation arm 854A (e.g., with about 7 lbs of force). The actuation arm 854A is connected to the roller clutch 858, which is a one-way roller clutch, such that retraction of the actuation arm 854A causes rotation of the one-way roller clutch 858. When the nitinol cools the return spring 854B presses on the opposite side of the roller clutch 858 such that the actuation arm 854A returns to the original position where the actuation arm 854A is able to be actuated again by activating the motor drive 854, generating a ratcheting effect. The drive shaft 860 is coupled to the roller clutch 858 such that ratcheting of the roller clutch ratchets the drive shaft 860.

The drive shaft 860 is adapted to be connected to the actuation head of one of the tensioners 20, such as the first tensioner 20A, for example, by including a suitable mating component, such as a hex head driver, or by being integrally formed or otherwise connected to the actuation head, such as the actuation head 78A (FIG. 3). In some embodiments, the housing 856 of the implantable driver 852 is secured to the housing 80A and/or the stabilizing member 12, for example being integrally formed therewith.

FIGS. 39, 40, and 41 show an expanding stabilizing member system 900 that is optionally employed in addition to, or as a replacement for, the stabilizing member 12. For example, the system 900, also described as a reciprocating adjuster and a resistance adjuster, is optionally employed by attaching the system 900 to the spinal column 24 (FIG. 1) using the stabilizing anchors 18, such that the spinal column 24 is able to be expanded longitudinally to help reduce the defective curvature of the spinal column 24.

In some embodiments, the system 900 includes a housing 902, a drive member 904, also described as a slide unit, a drive spring 906, also described as a potential energy drive, and a magnetic walker assembly 908, also described as a resistance unit. The drive member 904 is optionally substantially cylindrical and includes a plurality of surface grooves 910 along the length of the drive member 904, the surface grooves 910 being adapted to mate with the magnetic walker assembly 908 which acts as both a piston and a return mechanism. In some embodiments, the drive spring 906 is received within the housing 902 between the end of the drive member 904 and the housing 902. The drive spring 906 is a compression spring for exerting a pushing force on the drive member 904. As shown, the drive member 904 extends from the housing 902, the drive member 904 being adapted to slide within the housing 902 when not restricted by the magnetic walker assembly 908.

In some embodiments, the magnetic walker assembly 908 is secured to the housing 902 and includes a first receptacle 916 holding a first toothed member 918 and a second receptacle 920 holding a second toothed member 922. Each of the first and second toothed members 918, 922 are biased in the downward position (e.g., by a spring—not shown), the first and second toothed members 918, 922 each including a plurality of teeth 918A, 922A for mating with the surface grooves 910. In some embodiments, each of the first and second toothed members displays a different polarity from the other. In some embodiments, each of the toothed members 918, 922 is substantially arcuately shaped to increase the surface engagement with the surface grooves 910.

An external magnet 930 having a first polarity portion 932 and a second, opposite polarity portion 934 is optionally employed through the skin to alternately actuate the first and second toothed members 918, 922 into and out of the surface grooves 910. In some embodiments, the effective length of the system 900 is adjusted by alternatively actuating the first and second toothed members 918, 922 to "walk" the drive member 904 outwardly from the housing 902, where the potential energy represented in the system 900 by the spring 906 is released as the toothed members 918, 922 engage and release the surface grooves 910. Although a spring is used in some embodiments, in other embodiments an expanding material, such as those previously described, is utilized to exert a pushing force on the drive member 904. FIGS. 40 and 41 are illustrative of the alternate engagement of the first toothed member, those figures showing the external magnet 930, the drive member 904, and the first toothed member 918 with other portions removed for ease of illustration. FIG. 40 shows the first toothed member 918 in an engaged position and FIG. 41 shows the external magnet 930 rotated 180 degrees such that the first toothed member 918 is actuated to a disengaged position.

Figure 42:
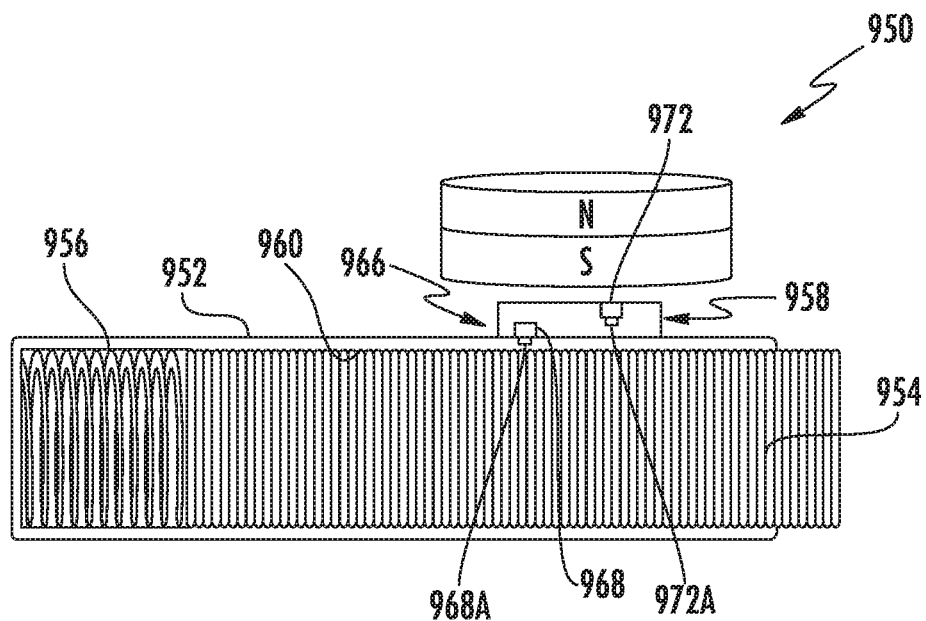
FIGS. 42, 43, and 44 show an expanding stabilizing member system that is optionally employed in addition to, or as a replacement for, the stabilizing member of the system of FIG. 1, according to some embodiments.
Figure 43:
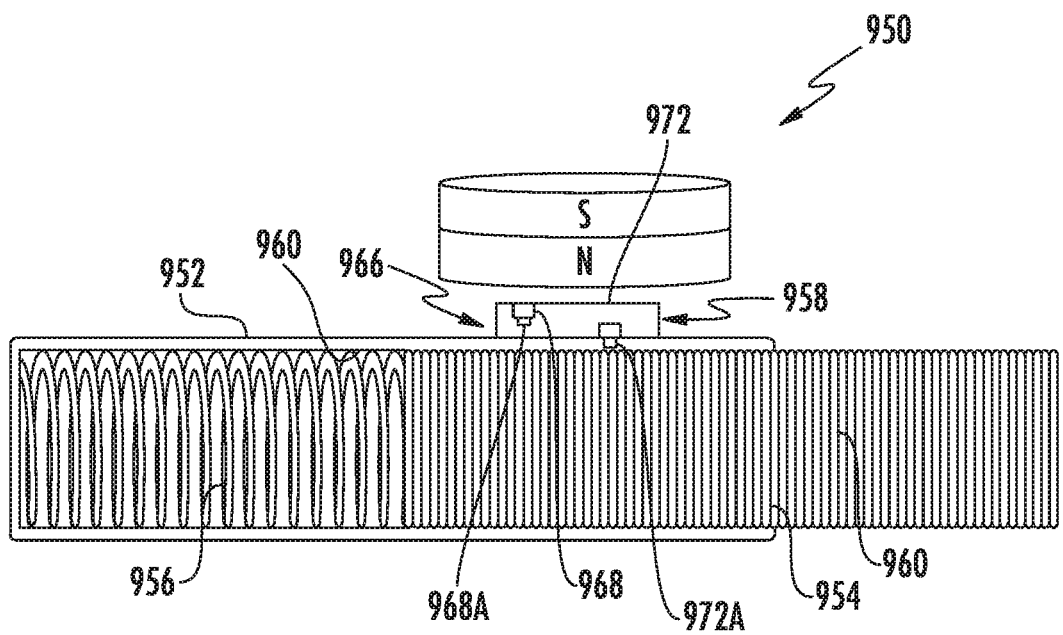

FIGS. 42 and 43 show another expanding stabilizing member system 950 that is optionally employed in addition to, or as a replacement for, the stabilizing member 12. For example, the system 950, also described as a reciprocating adjuster and a resistance adjuster, is optionally employed by attaching the system 950 to the spinal column 24 (FIG. 1) using the stabilizing anchors 18, such that the spinal column 24 is able to be expanded longitudinally using the system 950 to help reduce the defective curvature of the spinal column 24.

Similarly to the system 900, in some embodiments, the system 950 includes a housing 952, a drive member 954, also described as a slide unit, a drive spring 956, also described as a potential energy drive, and a magnetic walker assembly 958, also described as a resistance unit, that acts as a drive piston and a return mechanism.

As shown, the magnetic walker assembly 958 is secured to the housing 952 and includes a receptacle 966 holding a first toothed member 968 and a second toothed member 972, the first and second toothed members 968, 972 being positioned on an arm that is hinged to the receptacle 966. Each of the first and second toothed members 968, 972 is biased in the downward position (e.g., by a spring—not shown), the first and second toothed members 968, 972 each including one or more teeth 968A, 972A for mating with the surface grooves 960. In some embodiments, each of the first and second toothed members 968, 970 is characterized by a different polarity from the other. In some embodiments, each of the toothed members 968, 972 is substantially arcuately shaped to increase the surface engagement with the surface grooves 960.

Figure 44:
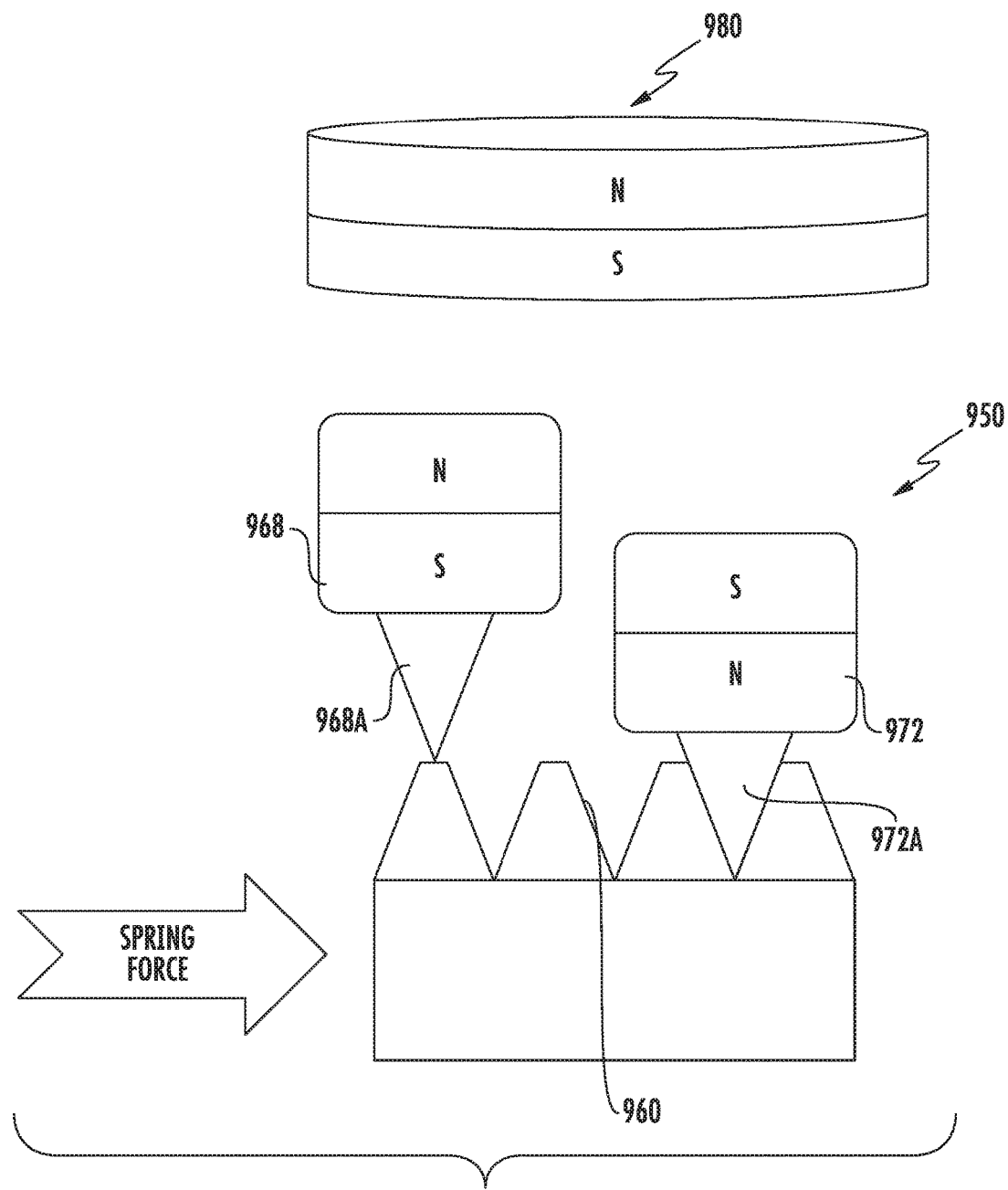

A principle of operation of the system 950 is illustrated more generally in FIG. 44. As shown, an external magnet 980 having a first polarity portion 982 and a second, opposite polarity portion 984 is optionally employed through the skin (not shown) to alternately actuate the first and second toothed members 968, 972 into and out of the surface grooves 960. In some embodiments, the effective length of the system 950 is adjusted by alternatively actuating the first and second toothed members 968, 972 to "walk" or "step" the drive member 954 outwardly from the housing 952, where the potential energy represented in the system 950 by the spring 956 is released as the toothed members 968, 972 alternately engage and release the surface grooves 960, the two members 968, 972 alternatively acting as piston unit and a return mechanism. Although a spring is used in some embodiments, in other embodiments an expanding material, such as those previously described, is utilized to exert a pushing force on the drive member 954. As an alternative to a physical magnet, the external magnet 980 is optionally an electric magnet that is able to switch polarities for stepping the system 950 at a desired electromagnetic force and speed.

Figure 45:
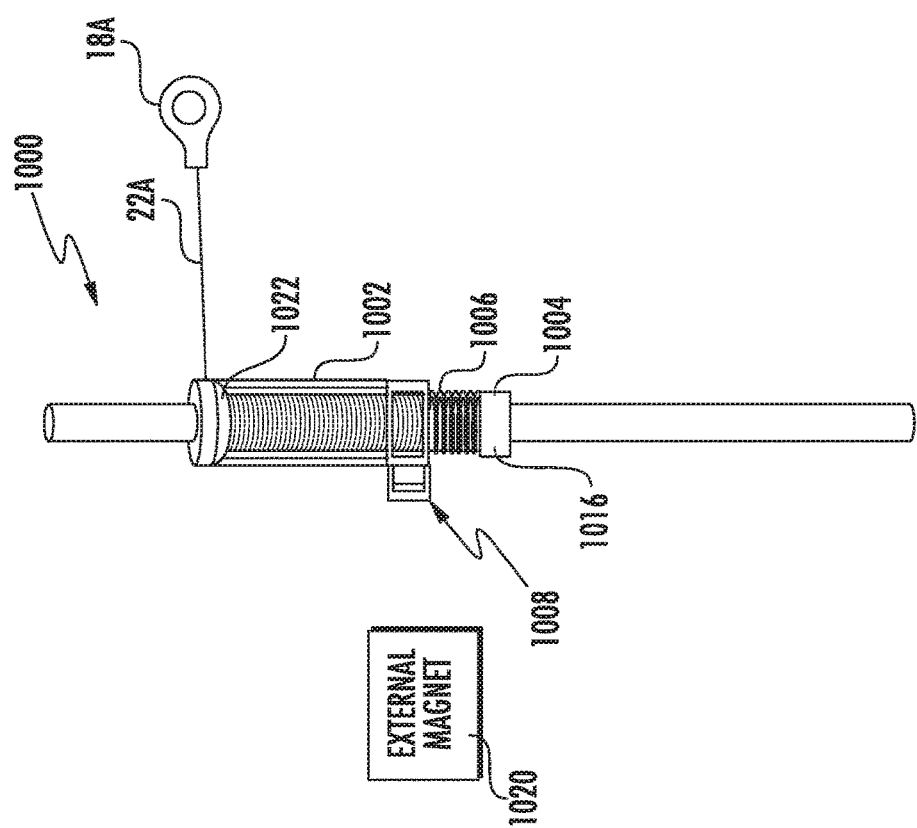
FIGS. 45 and 46 show another tensioning system that is optionally employed in addition to, or as a replacement for, one or more of the tensioners, according to some embodiments.
Figure 46:
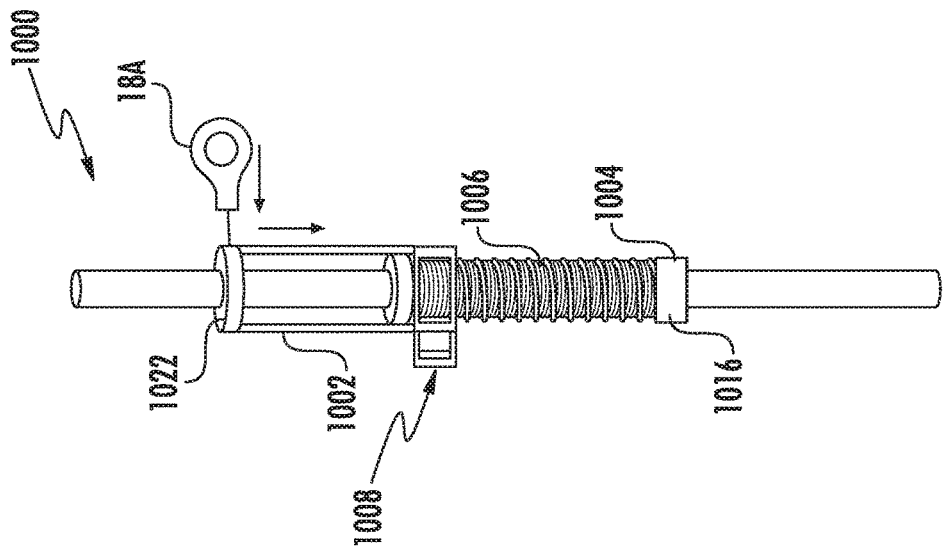

Some embodiments apply the magnetic stepping, or walking, operation described in association with systems 900 and 950 for another tensioning system 1000 shown in FIGS. 45 and 46, the system 1000 being optionally employed in addition to, or as a replacement for, one or more of the tensioners 20. As shown, the system 1000, also described as a reciprocating adjuster and a resistance adjuster, includes a housing 1002, a drive member 1004, also described as a slide unit, a drive spring 1006, also described as a potential energy drive, and a magnetic walker assembly 1008, also described as a resistance unit. The drive member 1004 is optionally configured with surface grooves similar to those of the systems 900 and 950 and the magnetic walker assembly 1008, acting as a piston unit and a return mechanism, is optionally adapted to interact with the drive member 1004 similarly to those of the systems 300, 900 and/or 950. Upon application of a magnetic force of alternating polarity (schematically indicated by external magnet 1020 in FIG. 44), the system 1000 operates similarly to the system 300 described above.

For example, the drive member 1004 is adapted to slide over the stabilizing member 12 while the housing 1002 is secured relative thereto, the drive member 1004 being able to slide out from the housing 1002 until an enlarged head 1020 of the drive member 1004 limits further travel of the drive member 1004. As shown, the drive spring 1006 is coaxially received over the drive member 1004 between the base 1016 and the housing 1002. The drive spring 1006 is a compression spring for exerting a pushing force on a base 1016 of the drive member 1004, to move the drive member 1004 from a first position (FIG. 45) to a second position (FIG. 46) away from the housing 1002, although other types of springs are contemplated.

One of the connectors 22, such as the first connector 22A is secured to an enlarged head 1022 of the drive member 1004. An aperture, roller, or other feature (not shown) is provided on the housing 1002 such that the connector 22A is able to extend outwardly, in a transverse direction from the housing 1002. As the drive member 1004 pistons downwardly out from the housing 1002, the enlarged head 1022 moves downwardly, pulling the first connector 22A into the housing 1002 and reducing the effective length of the first connector 22A between the stabilizing member 12 and the first correction anchor 18A, for example.

According to the foregoing, various embodiments relate to a spinal correction system for implantation in a patient, the system including a correction anchor, a stabilizing member, a reciprocating adjuster, and a connector. The correction anchor is configured to be secured to a vertebra in a defect area of a spine. The stabilizing member is configured to be secured against translation at the defect area of the spine. The reciprocating adjuster is coupled to the stabilizing member, the reciprocating adjuster including: a piston unit displaceable in a first direction, and a transfer unit coupled to the piston unit such that displacement of the piston unit in the first direction causes the transfer unit to be displaced in a second direction. The connector extends from the reciprocating adjuster to define an effective length between the reciprocating adjuster and the correction anchor, the connector having a first end configured to be coupled to the transfer unit and a second end configured to be coupled to the correction anchor such that displacement of the transfer unit causes shortening of the effective length of the connector.

In some embodiments, the piston unit includes a depressible shaft and the transfer unit includes a roller.

In some embodiments, the roller is a one-way drive clutch.

In some embodiments, the system is configured such that displacement of the roller winds the connector about the roller.

In some embodiments, the piston unit includes gearing and the transfer unit includes gearing for mating with the gearing of the piston unit.

In some embodiments, the piston unit includes a tooth member and the transfer unit includes a plurality of surface grooves configured to mate with the tooth member such that, upon displacement of the piston unit, the tooth member mates with the groove to displace the transfer unit.

In some embodiments, the piston unit is displaceable between a first position and a second position and the piston unit includes a return mechanism for returning the piston unit from the second position to the first position.

In some embodiments, the return mechanism includes a spring.

In some embodiments, the piston unit is coupled to a magnetic member.

In some embodiments, the system further comprises an external magnetic drive for actuating the piston unit by displacing the magnetic member.

In some embodiments, the system further comprises an implantable motor and an implantable power source, the motor being coupled to the piston unit.

In some embodiments, the power source includes an internal antennae for receiving inductive power.

In some embodiments, the power source includes an implantable battery.

According to the foregoing, various embodiments relate to a method of correcting a spine, the method including securing a correction anchor to a vertebra in a defect area of a spine and securing a stabilizing member against translation at the defect area of the spine. A piston unit of a reciprocating adjuster is displaced in a first direction to cause a transfer unit of the reciprocating adjuster to be displaced in a second direction, in turn, causing shortening of an effective length of a connector coupling the correction anchor and the reciprocating adjuster.

According to the foregoing, various embodiments relate to a spinal correction system for implantation in a patient, the system including a correction anchor, a stabilizing member, a resistance adjuster, and a connector. The correction anchor is configured to be secured to a vertebra in a defect area of a spine. The stabilizing member is configured to be secured against translation at the defect area of the spine. The resistance adjuster is coupled to the stabilizing member, the resistance adjuster including: a potential energy drive, a slide unit coupled to the potential energy drive such that the potential energy drive exerts a displacement force on the slide unit biasing the slide unit in a first direction, and a resistance unit coupled to the slide unit, the resistance unit being configured to selectively oppose the displacement force. The connector extends from the resistance adjuster to define an effective length between the resistance adjuster and the correction anchor, the connector having a first end configured to be coupled to the slide unit and a second end configured to be coupled to the correction anchor such that displacement of the slide unit in the first direction causes shortening of the effective length of the connector.

In some embodiments, the potential energy drive is received coaxially about the slide unit.

In some embodiments, the resistance unit includes a tooth member and the slide unit includes a plurality of surface grooves configured to mate with the tooth member such that upon displacing the tooth member longitudinally from a first position to a second position releases the resistance unit.

In some embodiments, the potential energy drive includes an expanding material.

In some embodiments, the expanding material is temperature activated.

In some embodiments, the expanding material is fluid activated.

In some embodiments, the potential energy drive includes a spring.

In some embodiments, the resistance unit includes hydrogel material.

In some embodiments, the resistance unit includes a biodegradable material.

In some embodiments, the resistance unit is coupled to a magnetic member.

In some embodiments, the system further comprises an external magnetic drive for actuating the slide unit by displacing the magnetic member.

In some embodiments, the external magnetic drive includes a rotating magnet.

In some embodiments, the system further comprises an implantable motor and an implantable power source, the motor being coupled to the piston unit.

In some embodiments, the power source includes an internal antennae for receiving inductive power.

In some embodiments, the power source includes an implantable battery.

According to the foregoing, various embodiments relate to a method of correcting a spine, the method including securing a correction anchor to a vertebra in a defect area of a spine and securing a stabilizing member against translation at the defect area of the spine. The method also includes actuating a resistance unit of a resistance adjuster coupled to the stabilizing member such that the resistance adjuster selectively releases a displacement force provided by a potential energy drive coupled to a slide unit, the slide unit being displaced by the potential energy drive in a first direction to cause shortening in an effective length of a connector coupled between the resistance adjuster and the correction anchor.

According to the foregoing, various embodiments relate to a spinal correction system for implantation in a patient, the system including a correction anchor, a stabilizing member, a resistance adjuster, and a connector. The correction anchor is configured to be secured to a vertebra in a defect area of a spine. The stabilizing member is configured to be secured against translation at the defect area of the spine. The resistance adjuster is coupled to the stabilizing member, the resistance adjuster including: a potential energy drive including an expanding material configured to expand after being subjected to an internal body environment of the patient and a slide unit coupled to the potential energy drive such that the potential energy drive exerts a displacement force on the slide unit biasing the slide unit in a first direction. The connector extends from the resistance adjuster to define an effective length between the resistance adjuster and the correction anchor, the connector having a first end configured to be coupled to the slide unit and a second end configured to be coupled to the correction anchor such that displacement of the slide unit in the first direction causes shortening of the effective length of the connector.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. A spinal correction system for implantation in a patient, the system comprising:
    a correction anchor configured to be secured to a vertebra in a defect area of a spine;
    a stabilizing member configured to be secured against translation at the defect area of the spine;
    a reciprocating adjuster coupled to the stabilizing member, the reciprocating adjuster including:
        a cap linearly displaceable between a first position and a second position;
        a return mechanism for returning the cap from the second position to the first position; and
        a transfer unit coupled to the cap such that displacement of the cap in the first direction causes the transfer unit to be displaced in a second direction; and
    a connector extending from the reciprocating adjuster to define an effective length between the reciprocating adjuster and the correction anchor, the connector having a first end configured to be coupled to the transfer unit and a second end configured to be coupled to the correction anchor such that displacement of the transfer unit causes shortening of the effective length of the connector.

2. The system of claim 1, wherein the transfer unit includes a roller and a drive shaft.

3. The system of claim 2, wherein displacement of the roller winds the connector about the roller.

4. A spinal correction system for implantation in a patient, the system comprising:
    a correction anchor configured to be secured to a vertebra in a defect area of a spine;
    a stabilizing member configured to be secured against translation at the defect area of the spine;
    a reciprocating adjuster coupled to the stabilizing member, the reciprocating adjuster including:

a cap displaceable between a first position and a second position;

a return mechanism for returning the cap from the second position to the first position; and a transfer unit coupled to the cap such that displacement of the cap in the first direction causes the transfer unit to be displaced in a second direction, the transfer unit including a roller and a drive shaft, the roller being a one-way drive clutch; and a connector extending from the reciprocating adjuster to define an effective length between the reciprocating adjuster and the correction anchor, the connector having a first end configured to be coupled to the transfer unit and a second end configured to be coupled to the correction anchor such that displacement of the transfer unit causes shortening of the effective length of the connector.

5. The system of claim 4, wherein the one-way drive clutch includes grooves or ridges.

6. A spinal correction system for implantation in a patient, the system comprising:

a correction anchor configured to be secured to a vertebra in a defect area of a spine;

a stabilizing member configured to be secured against translation at the defect area of the spine;

a reciprocating adjuster coupled to the stabilizing member, the reciprocating adjuster including:

a cap displaceable between a first position and a second position;

a return mechanism for returning the cap from the second position to the first position, the return mechanism including a spring; and a transfer unit coupled to the cap such that displacement of the cap in the first direction causes the transfer unit to be displaced in a second direction; and a connector extending from the reciprocating adjuster to define an effective length between the reciprocating adjuster and the correction anchor, the connector having a first end configured to be coupled to the transfer unit and a second end configured to be coupled to the correction anchor such that displacement of the transfer unit causes shortening of the effective length of the connector.

\* \* \* \* \*